(12) United States Patent
Barker

(10) Patent No.: US 10,946,186 B2
(45) Date of Patent: Mar. 16, 2021

(54) SYSTEMS AND METHODS FOR MAKING AND USING A LEAD INTRODUCER WITH A SEAL FOR AN ELECTRICAL STIMULATION SYSTEM

(71) Applicant: Boston Scientific Neuromodulation Corporation, Valencia, CA (US)

(72) Inventor: John M. Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 120 days.

(21) Appl. No.: 16/246,355

(22) Filed: Jan. 11, 2019

(65) Prior Publication Data

US 2019/0143099 A1    May 16, 2019

Related U.S. Application Data

(63) Continuation of application No. 15/139,149, filed on Apr. 26, 2016, now Pat. No. 10,226,616.
(Continued)

(51) Int. Cl.
*A61N 1/05* (2006.01)
*A61B 17/34* (2006.01)
(Continued)

(52) U.S. Cl.
CPC ............ *A61N 1/05* (2013.01); *A61B 17/3468* (2013.01); *A61B 17/3417* (2013.01);
(Continued)

(58) Field of Classification Search
CPC ....... A61N 1/05; A61N 1/0551; A61M 25/06; A61B 17/3417; A61B 17/3468
See application file for complete search history.

(56) References Cited

U.S. PATENT DOCUMENTS

| 3,330,278 A | 7/1967 | Santomieri |
| 3,359,978 A | 12/1967 | Smith |

(Continued)

FOREIGN PATENT DOCUMENTS

| EP | 2008686 | 12/2008 |
| WO | 89/00436 | 1/1989 |
| WO | 03011361 | 2/2003 |

OTHER PUBLICATIONS

U.S. Appl. No. 62/116,018, filed Feb. 13, 2015.
(Continued)

*Primary Examiner* — Tuan V Nguyen
(74) *Attorney, Agent, or Firm* — Branch Partners PLLC; Bruce E. Black

(57) ABSTRACT

One embodiment is a lead introducer including an outer needle, an inner needle, a splittable member, and an annular seal member. The outer needle, inner needle, and splittable member each include a body and hub. The splittable member fits over the outer needle body and the inner needle body and can be separated longitudinally. The splittable member hub receives at least portions of both the inner needle hub and the outer needle hub within the splittable member hub. The annular seal member is formed by either a) the inner needle hub or b) a combination of the inner needle hub and outer needle hub. The annular seal member forms a fluid-resisting seal with the interior surface of the splittable member hub when the portions of the inner needle hub and outer needle hub are received within the splittable member hub.

20 Claims, 16 Drawing Sheets

Related U.S. Application Data

(60) Provisional application No. 62/153,844, filed on Apr. 28, 2015.

(51) Int. Cl.
*A61B 90/00* (2016.01)
*A61M 25/06* (2006.01)

(52) U.S. Cl.
CPC .. *A61B 2090/3966* (2016.02); *A61M 25/0668* (2013.01); *A61N 1/0551* (2013.01)

(56) References Cited

U.S. PATENT DOCUMENTS

| | | |
|---|---|---|
| 3,568,660 A | 3/1971 | Crites et al. |
| 3,677,243 A | 7/1972 | Nerz |
| 4,166,469 A | 9/1979 | Littleford |
| 4,355,646 A | 10/1982 | Kallok et al. |
| 4,449,973 A | 5/1984 | Luther |
| RE31,855 E | 3/1985 | Osborne |
| 4,512,351 A | 4/1985 | Pohndorf |
| 4,608,986 A | 9/1986 | Beranek et al. |
| 4,808,157 A | 2/1989 | Coombs |
| 5,125,904 A | 6/1992 | Lee |
| 5,312,355 A | 5/1994 | Lee |
| 5,320,602 A | 6/1994 | Karpiel |
| 5,380,290 A | 1/1995 | Makower et al. |
| 5,409,469 A | 4/1995 | Schaerf |
| 5,441,504 A | 8/1995 | Pohndorf et al. |
| 5,713,867 A | 2/1998 | Morris |
| 5,741,233 A | 4/1998 | Riddle et al. |
| 5,752,937 A | 5/1998 | Otten et al. |
| 5,755,693 A | 5/1998 | Walker et al. |
| 5,931,863 A | 8/1999 | Griffin, III et al. |
| 6,080,141 A | 6/2000 | Castro et al. |
| 6,181,969 B1 | 1/2001 | Gord |
| 6,251,119 B1 | 6/2001 | Addis |
| 6,358,460 B1 | 3/2002 | Hunt, Jr. et al. |
| 6,454,744 B1 | 9/2002 | Spohn et al. |
| 6,494,860 B2 | 12/2002 | Rocamora et al. |
| 6,516,227 B1 | 2/2003 | Meadows et al. |
| 6,582,390 B1 | 6/2003 | Sanderson |
| 6,609,029 B1 | 8/2003 | Mann et al. |
| 6,609,032 B1 | 8/2003 | Woods et al. |
| 6,641,564 B1 | 11/2003 | Kraus |
| 6,645,178 B1 | 11/2003 | Junker et al. |
| 6,712,791 B2 | 3/2004 | Lui et al. |
| 6,741,892 B1 | 5/2004 | Meadows et al. |
| 6,749,600 B1 | 6/2004 | Levy |
| 6,758,854 B1 | 7/2004 | Butler et al. |
| 6,869,416 B2 | 3/2005 | Windheuser et al. |
| 6,939,327 B2 | 9/2005 | Hall et al. |
| 7,001,396 B2 | 2/2006 | Glazier et al. |
| 7,014,626 B2 | 3/2006 | Sanderson |
| 7,101,353 B2 | 9/2006 | Lui et al. |
| 7,192,433 B2 | 3/2007 | Osypka et al. |
| 7,244,150 B1 | 7/2007 | Brase |
| 7,359,755 B2 | 4/2008 | Jones et al. |
| 7,437,193 B2 | 10/2008 | Parramon |
| 7,524,305 B2 | 4/2009 | Moyer |
| 7,672,734 B2 | 3/2010 | Anderson |
| 7,744,571 B2 | 6/2010 | Fisher et al. |
| 7,761,165 B1 | 7/2010 | He |
| 7,887,733 B2 | 2/2011 | Moyer |
| 7,909,798 B2 | 3/2011 | Osypka |
| 7,938,806 B2 | 5/2011 | Fisher et al. |
| 7,941,227 B2 | 5/2011 | Barker |
| 7,949,395 B2 | 5/2011 | Kuzma |
| 7,974,706 B2 | 7/2011 | Moffitt et al. |
| 7,985,232 B2 | 7/2011 | Potter et al. |
| 7,993,305 B2 | 8/2011 | Ye et al. |
| 8,043,263 B2 | 10/2011 | Helgeson et al. |
| 8,105,287 B2 | 1/2012 | Fisher et al. |
| 8,105,315 B2 | 1/2012 | Johnson et al. |
| 8,112,159 B2 | 2/2012 | Harris et al. |
| 8,137,317 B2 | 3/2012 | Osypka |
| 8,147,456 B2 | 4/2012 | Fisher et al. |
| 8,175,710 B2 | 5/2012 | He |
| 8,224,450 B2 | 7/2012 | Brase |
| 8,273,059 B2 | 9/2012 | Nardeo et al. |
| 8,348,899 B2 | 1/2013 | Chesnin et al. |
| 8,364,278 B2 | 1/2013 | Pianca et al. |
| 8,377,006 B2 | 2/2013 | Tal et al. |
| 8,382,715 B2 | 2/2013 | Nardeo et al. |
| 8,849,422 B2 | 9/2014 | Pianca |
| 2002/0111617 A1 | 8/2002 | Cosman et al. |
| 2005/0021119 A1 | 1/2005 | Sage et al. |
| 2005/0055027 A1 | 3/2005 | Yeung et al. |
| 2005/0107861 A1 | 5/2005 | Harris et al. |
| 2005/0113860 A1 | 5/2005 | Keidar |
| 2007/0150036 A1 | 6/2007 | Anderson |
| 2008/0300538 A1* | 12/2008 | Schweikert ....... A61M 25/0097 604/99.04 |
| 2009/0248111 A1 | 10/2009 | Pianca et al. |
| 2009/0254019 A1 | 10/2009 | Gehl et al. |
| 2009/0259283 A1 | 10/2009 | Brandt et al. |
| 2011/0054402 A1 | 3/2011 | Tanabe et al. |
| 2011/0218549 A1 | 9/2011 | Barker |
| 2011/0224680 A1 | 9/2011 | Barker |
| 2011/0224681 A1 | 9/2011 | McDonald |
| 2011/0230893 A1 | 9/2011 | Barker |
| 2012/0202928 A1 | 8/2012 | Barker et al. |
| 2012/0323254 A1 | 12/2012 | Bonde et al. |
| 2013/0053851 A1 | 2/2013 | Schmitz et al. |
| 2014/0039586 A1 | 2/2014 | Barker et al. |
| 2014/0073926 A1 | 3/2014 | Rajendran et al. |
| 2014/0276927 A1 | 9/2014 | Barker |
| 2015/0073431 A1 | 3/2015 | Barker |
| 2015/0073432 A1 | 3/2015 | Barker |

OTHER PUBLICATIONS

International Search Report and Written Opinion for PCT/US2016/029373 dated Aug. 26, 2016.

Official Communication for U.S. Appl. No. 15/139,149 dated May 22, 2018.

* cited by examiner

SYSTEMS AND METHODS FOR MAKING AND USING A LEAD INTRODUCER WITH A SEAL FOR AN ELECTRICAL STIMULATION SYSTEM

CROSS-REFERENCE TO RELATED APPLICATIONS

This application is a continuation of U.S. patent application Ser. No. 15/139,149, filed Apr. 26, 2016, which claims the benefit under 35 U.S.C. § 119(e) of U.S. Provisional Patent Application Ser. No. 62/153,844, filed Apr. 28, 2015, both of which are incorporated herein by reference.

FIELD

The present invention is directed to the area of implantable electrical stimulation systems and methods of making and using the systems. The present invention is also directed to a lead introducer for facilitating insertion of implantable electrical stimulation leads into patients, as well as methods of making and using the lead introducers and electrical stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead introducer including an outer needle, an inner needle, a splittable member, and an annular seal member. The outer needle includes an outer needle body and an outer needle hub. The outer needle body defines an open channel extending along the entire longitudinal length of the outer needle body. The inner needle includes an inner needle body for sliding along the open channel of the outer needle and an inner needle hub. The inner needle body defines a lumen extending along the entire longitudinal length of the inner needle body. The splittable member includes a splittable member body and a splittable member hub. The splittable member fits over the outer needle body and the inner needle body and is longitudinally splittable. The splittable member hub receives at least portions of both the inner needle hub and the outer needle hub within the splittable member hub. The annular seal member is formed by either a) the inner needle hub or b) a combination of the inner needle hub and outer needle hub. The annular seal member forms a fluid-resisting seal with the interior surface of the splittable member hub when the portions of the inner needle hub and outer needle hub are received within the splittable member hub.

Another embodiment is a lead introducer including an outer needle, an inner needle, and a splittable member. The outer needle includes an outer needle body and an outer needle hub. The outer needle body defines an open channel extending along the entire longitudinal length of the outer needle body. The inner needle includes an inner needle body for sliding along the open channel of the outer needle and an inner needle hub. The inner needle body defines a lumen extending along the entire longitudinal length of the inner needle body. The splittable member includes a splittable member body and a splittable member hub. The splittable member fits over the outer needle body and the inner needle body and is longitudinally splittable. The splittable member hub receives at least portions of both the inner needle hub and the outer needle hub within the splittable member hub. The splittable member hub includes two pull-apart tabs extending proximally from the splittable member body in a direction parallel to the longitudinal axis of the splittable member. The splittable member is configured for separating longitudinally by pulling the two pull-apart tabs away from each other.

In at least some embodiments, the preceding lead introducer also includes an annular seal member formed by either a) the inner needle hub or b) a combination of the inner needle hub and outer needle hub, where the annular seal member is configured and arranged to form a fluid-resisting seal with the interior surface of the splittable member hub when the portions of the inner needle hub and outer needle hub are received within the splittable member hub.

In at least some embodiments of any of these lead introducers, the annular seal member includes an O-ring disposed along a distal portion of the inner needle hub. In at least some embodiments of any of these lead introducers, the outer needle hub defines an annular detent and the splittable member hub includes a ridged structure configured and arranged to mate with the annular detent.

In at least some embodiments of any of these lead introducers, the inner needle hub includes a seal element including a wedge and a partial seal rib defined at a distal end of the wedge. In at least some embodiments of any of these lead introducers, the outer needle hub further includes a seal rib that, when mated with the partial seal rib of the inner needle hub, forms the annular seal member. In at least some embodiments of any of these lead introducers, the outer needle hub defines a wedge-shaped opening configured and arranged to mate with the wedge of the seal element of the inner needle hub. In at least some embodiments of any of these lead introducers, the seal element of the inner needle hub has a conical shape except for the wedge.

In at least some embodiments of any of these lead introducers, the inner needle hub includes a collar defining two openings, where the two openings are configured and arranged to receive a portion of the two pull-apart tabs within the two openings to prevent inadvertently pulling the two pull-apart tabs away from each other. In at least some embodiments of any of these lead introducers, the outer needle hub includes a collar defining two openings, where the two openings are configured and arranged to receive a portion of the two pull-apart tabs within the two openings to prevent inadvertently pulling the two pull-apart tabs away from each other.

In at least some embodiments of any of these lead introducers, the lead introducer further includes a stylet including a stylet body and a stylet hub coupled to the stylet body, where the stylet body is configured and arranged for sliding along the lumen of the inner needle body and the stylet hub includes projections disposed on a distal portion of the stylet hub and defining cavities to receive a portion of the two pull apart tabs.

In at least some embodiments of any of these lead introducers, the splittable member includes a radiopaque marker disposed at or near the distal end of the splittable member.

Yet another embodiment is an insertion kit including any of the lead introducers described above; and a neurostimulation lead configured and arranged for implantation into a patient. The neurostimulation lead includes a lead body having a distal end portion and a proximal end portion, electrodes disposed at the distal end portion of the lead body, terminals disposed at the proximal end portion of the lead body, and conductive wires coupling the electrodes electrically to the terminals. The open channel of the outer needle body is configured and arranged such that, when the inner needle of the lead introducer is not inserted in the open channel, the distal end portion of the lead body is insertable into the open channel with the lead body being laterally separatable from the outer needle of the lead introducer through the open channel of the outer needle body.

A further embodiment is an electrical stimulation system including the insertion kit describe above and a control module to electrically couple to the neurostimulation lead of the insertion kit. The control module includes a housing, an electronic subassembly disposed in the housing, and a connector for receiving the neurostimulation lead. The connector includes a connector housing defining a port for receiving the proximal end portion of the lead body, and connector contacts disposed in the connector housing, the connector contacts configured and arranged to couple to the terminals of the neurostimulation lead when the proximal end portion of the neurostimulation lead is received by the connector housing.

Another embodiment is a method of implanting a neurostimulation lead into a patient. The method includes advancing any one of the lead introducers describe above into the patient; removing the inner needle of the lead introducer from the patient, leaving the outer needle and splittable member of the lead introducer within the patient; inserting into the open channel of the outer needle body a distal end portion of a neurostimulation lead; separating the splittable member into at least two parts along the length of the lumen of the splittable member; and removing the outer needle and the splittable member from the patient, leaving the neurostimulation lead implanted in the patient at the target stimulation location.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a lead introducer for facilitating insertion of implantable electrical stimulation leads into patients, as well as methods of making and using the lead introducers and electrical stimulation leads.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
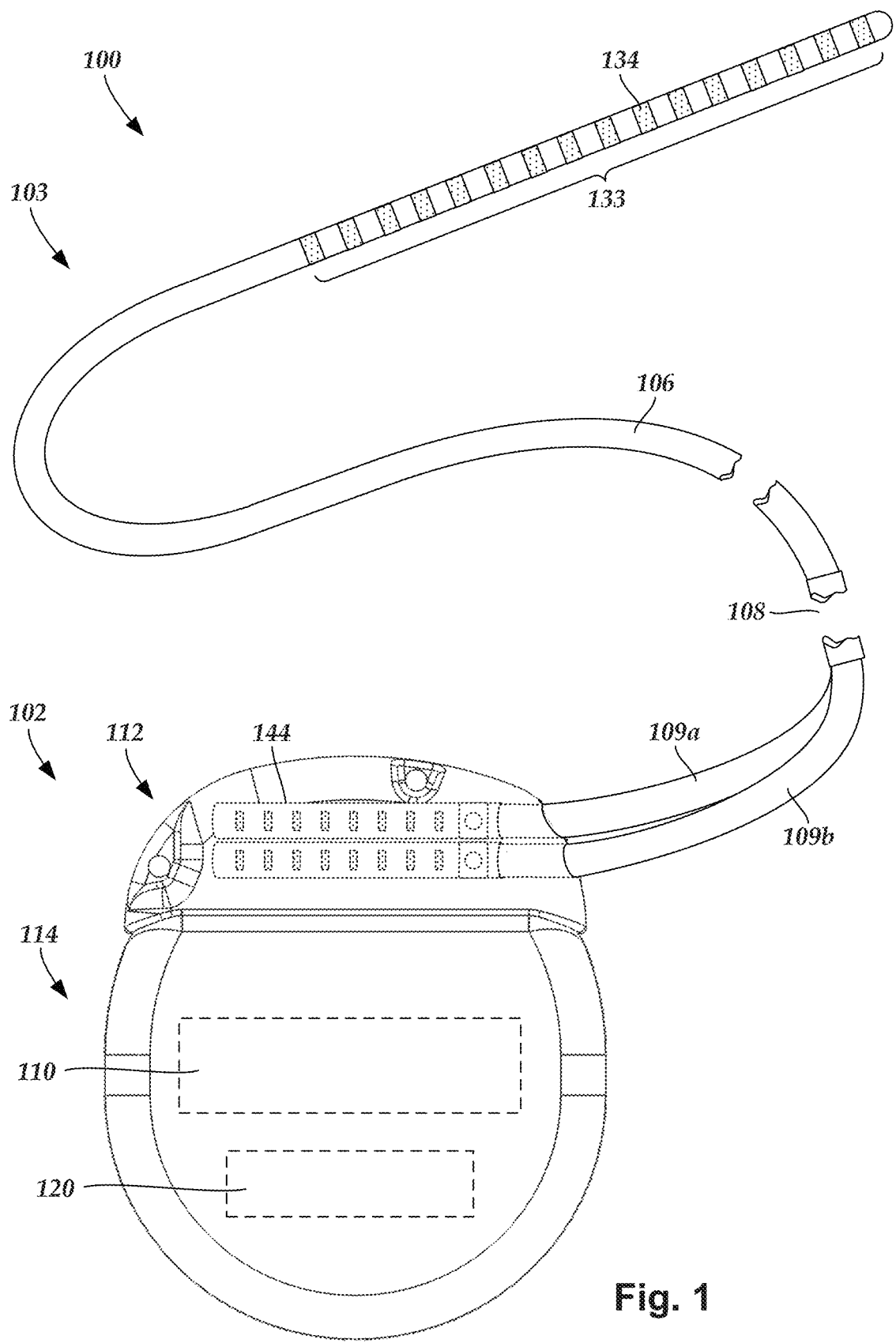
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106. In FIG. 1, the electrical stimulation system 100 is shown having a junction 108 configured to couple to distal portion of the lead 103 to one or more proximal portions 109a and 109b.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
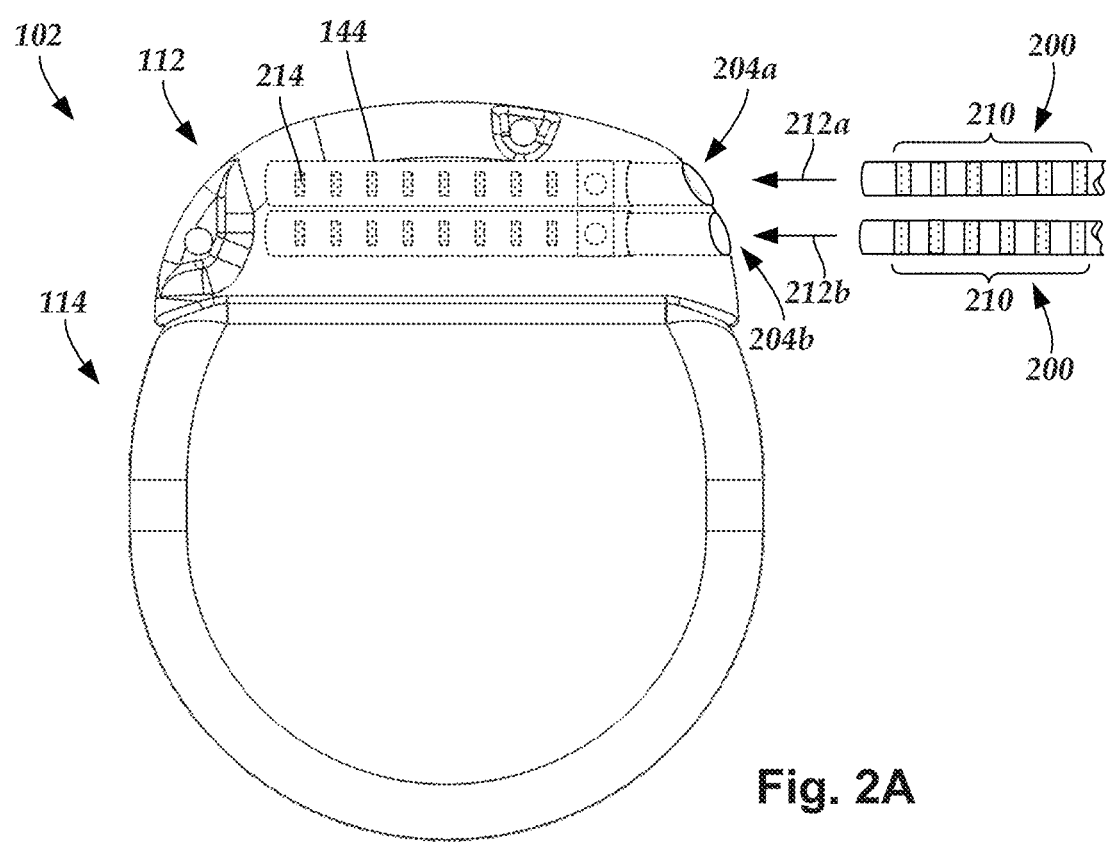
FIG. 2A is a schematic view of one embodiment of a proximal portion of a lead and a control module of an electrical stimulation system, according to the invention.
Figure 2B:
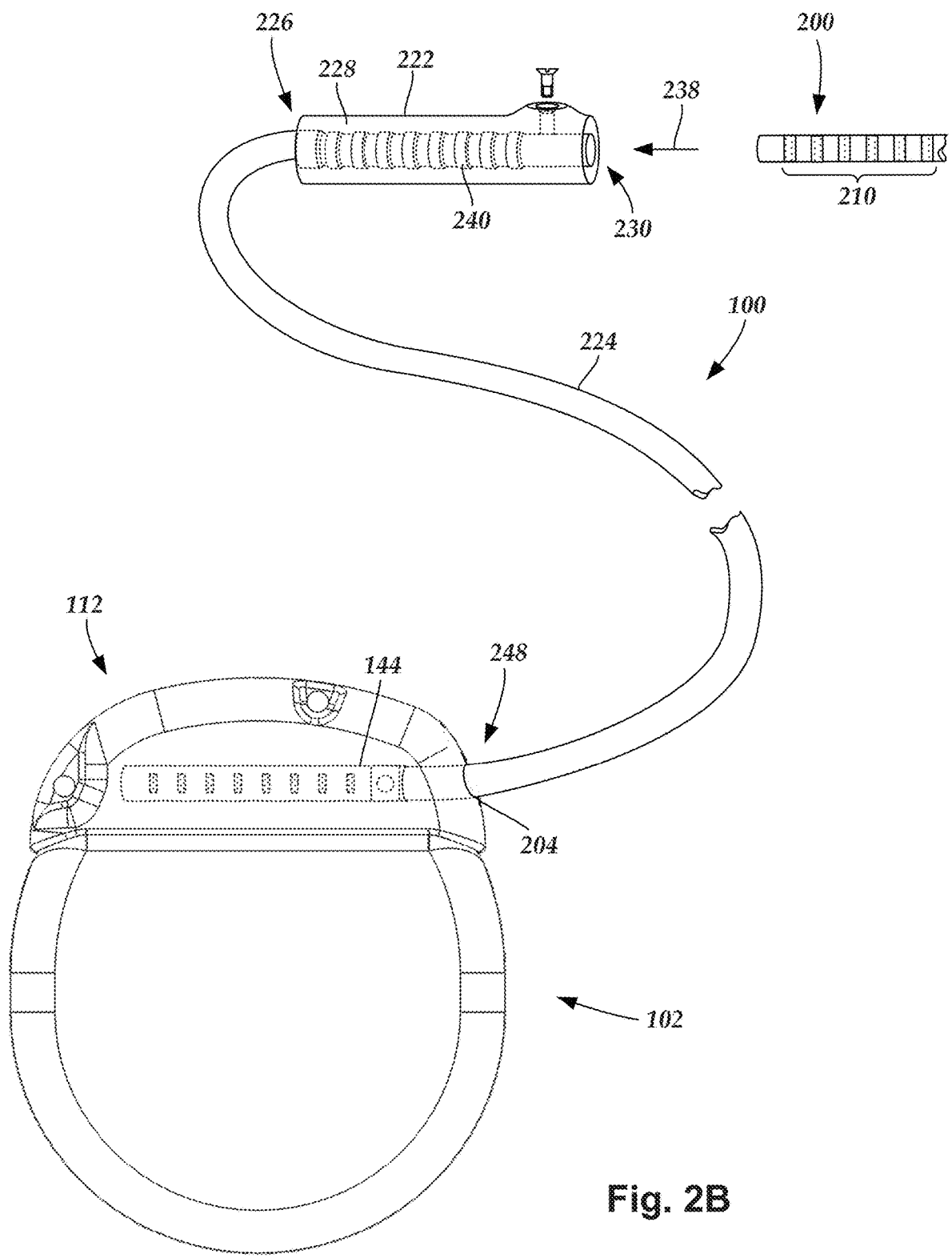
FIG. 2B is a schematic view of one embodiment of a proximal portion of a lead and a lead extension of an electrical stimulation system, according to the invention.

Terminals (e.g., 210 in FIGS. 2A-2B) are typically disposed along the proximal end of the one or more proximal portions of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 3:
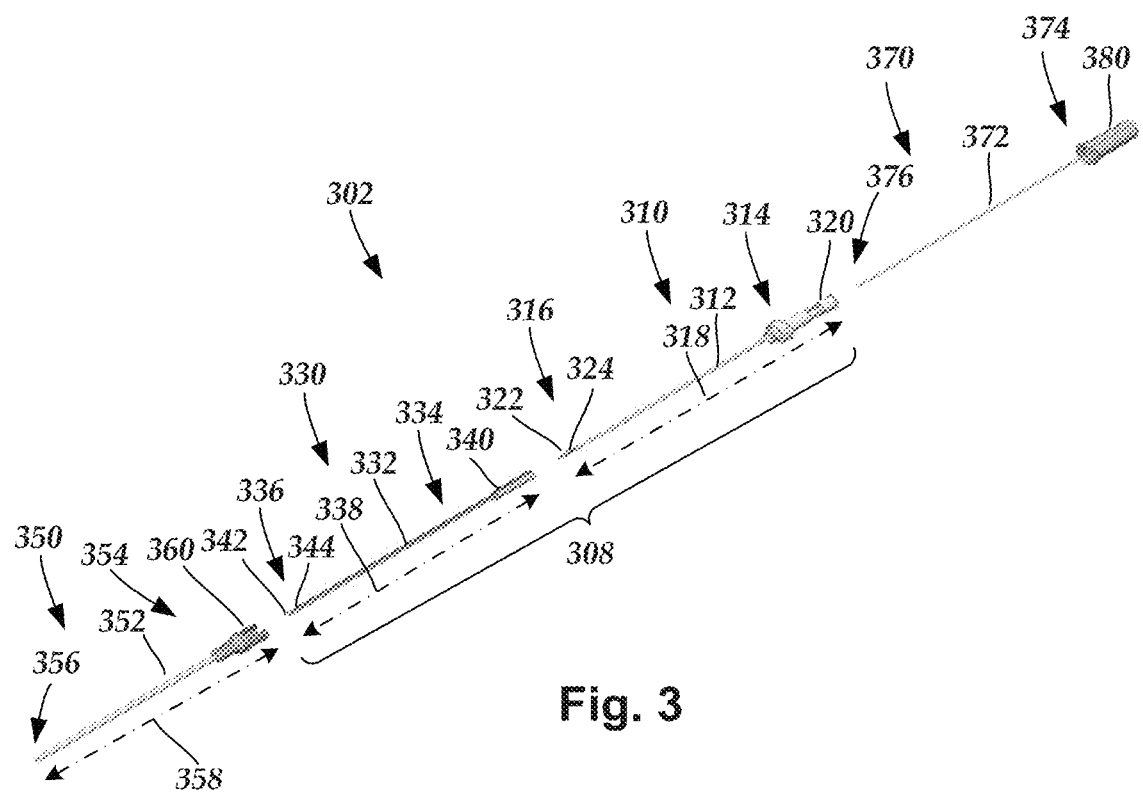
FIG. 3 is a schematic perspective exploded view of one embodiment of a lead introducer configured and arranged for facilitating implantation of a lead of an electrical stimulation system into a patient, the lead introducer including a multi-piece insertion needle, a splittable member, and an optional stylet, according to the invention.

Turning to FIG. 3, some conventional percutaneous implantation techniques involve inserting a lead introducer, such as an epidural needle, into a patient. Once the lead introducer is inserted into the patient, a lead is inserted into the lead introducer and the lead introducer is positioned at a target stimulation location. Once the lead is positioned at the target stimulation location, the lead introducer is removed from the patient, leaving the lead in place. Typically, the lead introducer is removed from the patient by sliding the lead introducer off the proximal end of the lead.

Unfortunately, when a lead has a body that is not isodiametric (such as the bifurcated lead shown in FIG. 1), it may be difficult to slide the lead introducer off the proximal end of the lead. For example, when a proximal end of a lead body has a diameter that is larger than a distal end of the lead body, or when an oversized junction or adapter is disposed along the length of the lead body, the varying diameters along the length of the lead body may hinder, or even prevent, the lead introducer from sliding off the proximal end of the lead.

A lateral release lead introducer ("lead introducer") uses a multi-piece insertion needle that enables a lead to be laterally separated from the multi-piece insertion needle. Examples of a lateral release lead introducer are found in, for example, U.S. Patent Applications Publication Nos. 2011/0224680, 2014/0039586, 2014/0276927, 2015/0073431, and 2015/0073432, all of which are incorporated by reference.

The lead introducer enables the lead to laterally separate from the multi-piece insertion needle without sliding the multi-piece insertion needle off the proximal end of the lead. In at least some embodiments, during implantation of the lead the multi-piece insertion needle is disposed in a splittable member that separates from the lead by splitting apart along a length of the splittable member.

It has been found, however, that in some lead introducers fluid can leak out of the introducer hub, particularly if the needle is relaxed or pulled back during insertion or when performing a "loss of resistance" check using a fluid-filled syringe for verifying epidural access. A leak path can be created between the needle and the sheath and can result in fluid emitting from a proximal hub assembly of the lead introducer. Including a seal within the proximal hub assembly can prevent or reduce this leakage.

Additionally or alternatively, the pull-apart tabs of the splittable member can be positioned parallel to the axis of the sheath as opposed to extending laterally as in other designs. This arrangement of the pull-apart tabs can provide for better access to the surgical site with less obstruction from the pull-apart tabs and can also prevent or reduce inadvertent, premature separation of the splittable member. The arrangement may also be useful when inserting two needles close to each other for implanting two or more leads.

FIG. 3 is a schematic perspective exploded view of one embodiment of a lead introducer 302 configured and arranged to facilitate implantation of an electrical stimulation system into a patient. The lead introducer 302 includes a multi-piece insertion needle 308 and a splittable member 350. The multi-piece insertion needle 308 includes an inner needle 310 that is insertable into an outer needle 330.

The inner needle 310 has a body 312 with a proximal end portion 314, a distal end portion 316, and a longitudinal length 318. The inner needle 310 includes a proximal hub 320 disposed along the proximal end portion 314 of the body 312 and a distal tip section 322 disposed along the distal end portion 316 of the body 312. In at least some embodiments, a bend is optionally formed along the distal end portion 316 proximal to the distal tip section 322. The inner needle 310 defines a lumen extending along the longitudinal length 318 of the inner needle 310.

The outer needle 330 has a body 332 with a proximal end portion 334, a distal end portion 336, and a longitudinal length 338. The outer needle 330 includes a proximal hub 340 disposed along the proximal end portion 334 of the body 332 and a distal tip section 342 disposed along the distal end portion 336 of the body 332. An optional bend 344 is formed along the distal end portion 334 of the body 332 proximal to the distal tip section 342. The outer needle 330 defines an open channel extending along the longitudinal length 338 of the outer needle 330 and the proximal hub 340.

The splittable member 350 has body 352, a proximal end portion 354, a distal end portion 356, and a longitudinal length 358. A proximal hub 360 is disposed along the proximal end portion 354. A lumen 355 (FIG. 7B) extends along the longitudinal length 356 of the splittable member 350 from the proximal hub 360.

The lead introducer 302 may additionally include one or more optional components, such as an optional stylet 370. The stylet 370 is insertable into the lumen of the inner needle 310. The stylet 370 has a body 372 with a proximal end portion 374 and an opposing distal end portion 376. A proximal hub 380 is disposed along the proximal end portion 374 of the body 372. In at least some embodiments, a distal tip of the distal end portion 376 of the stylet 370 is blunt to prevent coring of patient tissue during insertion of the lead introducer 302 into a patient. In at least some embodiments, a distal tip of the distal end portion 376 of the stylet 370 is slanted to conform to a beveled distal tip of the inner needle, the outer needle, or both.

In at least some other embodiments, the lead introducer 302 is suitable for use without the stylet 370. For example, in at least some embodiments the lumen (526 in FIG. 5) of the inner needle 310 has a diameter that is small enough to prevent coring of patient tissue without the use of the stylet 370. Tissue coring is typically undesirable. In addition to causing patient trauma, tissue plugged in the lumen of the inner needle may prevent a medical practitioner from being able to perform a loss-of-resistance technique to confirm epidural access.

The stylet 370 is formed from any suitable material including, for example, a flexible plastic resin (e.g., nylon, polyester, polyurethane, or the like), stainless steel, or the like. The stylet 370 is designed to be sufficiently rigid to be insertable through the lumen (526 in FIG. 5) of the inner needle 310, yet sufficiently flexible to navigate across the optional bend in the inner needle 310 when the inner needle 310 is nested with the outer needle 330. In at least some embodiments, the stylet 370 is configured to engage with the inner needle 310 to circumferentially align the distal tip of the stylet with the distal tip of the inner needle. For example, in at least some embodiments the proximal hub of either the stylet or the inner needle has a male feature that can be aligned with a female feature of the other of the stylet or inner needle by rotating either relative to the other. It may be advantageous to circumferentially align the stylet with the inner needle in order to align the beveled distal tip of the stylet with the beveled distal tip of the inner needle.

Alternately or additionally, the lumen of the inner needle 310 can be used to check for precise positioning of the lead introducer 302 during, for example, a loss-of-resistance test. In at least some embodiments, the proximal hub 320 of the inner needle 310 is suitable for receiving a syringe by incorporation of a Luer taper or other arrangement to provide a leak-free interface. In at least some embodiments, fluid (e.g., saline solution, air, or the like) may be introduced to, or removed from, the patient, via the lumen, to check for precise positioning of the lead introducer 302, for example, whether or not the epidural space has been entered.

The inner needle 310, the outer needle 330, and the splittable member 350, illustrated in FIG. 3, are coupleable to one another such that the inner needle 310, the outer needle 330, and the splittable member 350 form a nested arrangement. In at least some embodiments, the stylet 370 is insertable into the lumen of the inner needle 310 to form a nested arrangement along with the outer needle 330 and the splittable member 350.

Figure 4:
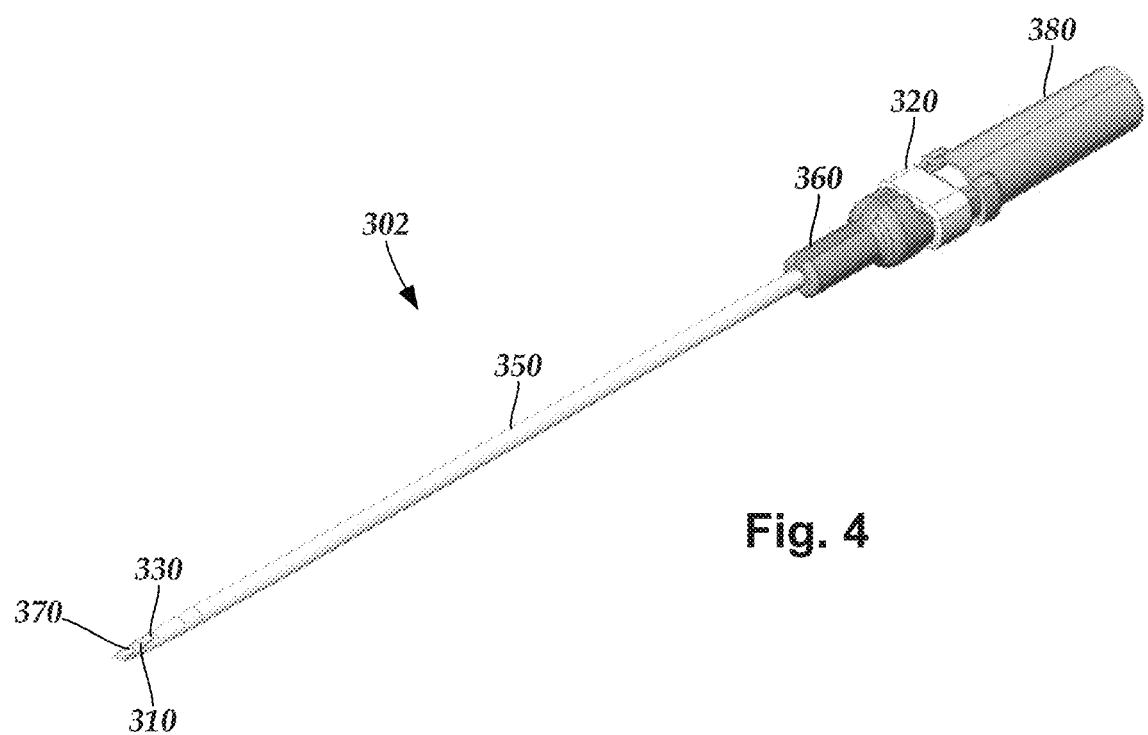
FIG. 4 is a schematic perspective view of one embodiment of the lead introducer of FIG. 3 with the multi-piece insertion needle and stylet nested in the splittable member of the lead introducer, according to the invention.

FIG. 4 is a schematic perspective view of this nested arrangement including the inner needle, outer needle, splittable member, and stylet such that the proximal hubs 320, 340 (not shown), 360, 380 of the inner needle 310, the outer needle 330, the splittable member 350, and the stylet 370, respectively, align axially to one another.

As discussed in more detail below with reference to FIG. 6A-6B, the inner needle 310 is disposed in the open channel of the outer needle. In at least some embodiments, the separation between the opposing edges of the open channel of the outer needle 330 is smaller than an outside diameter of the inner needle 310. In which case, the inner needle 310 does not separate laterally from the open channel of the outer needle 330, even when the outer needle 330 is not retained by the splittable member 350. Alternately, the inner needle 310 can be formed to separate from the outer needle 330 when not retained in the open channel of the outer needle 330 by the splittable member 350.

Figure 5:
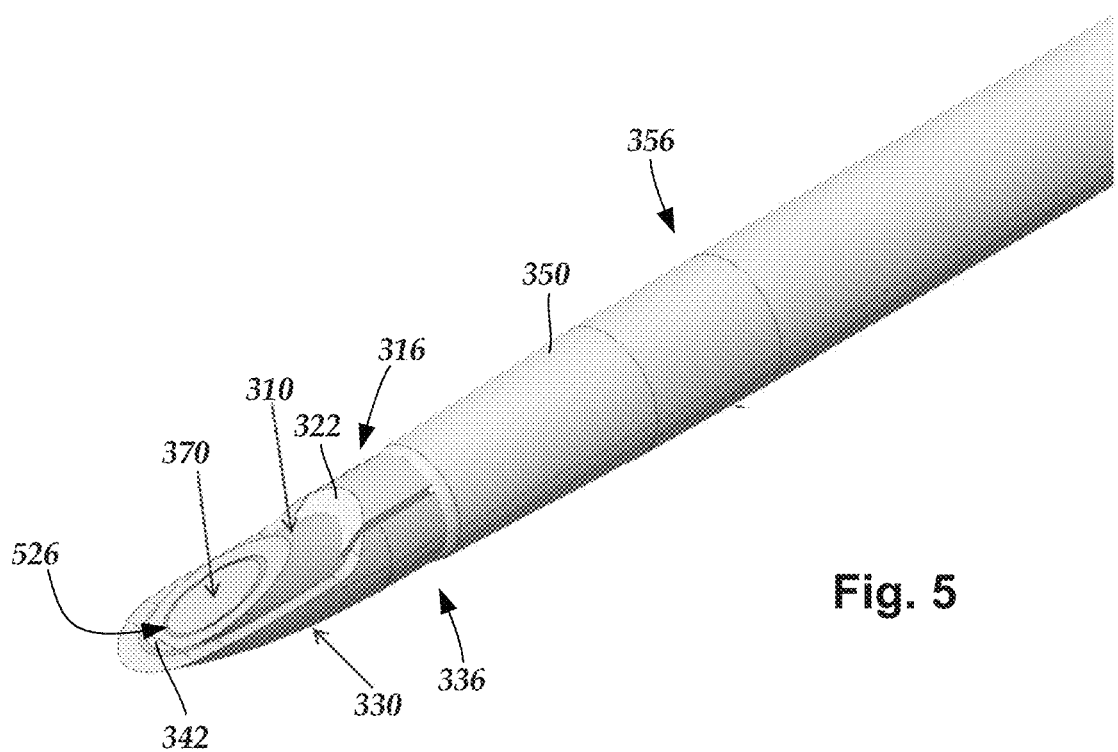
FIG. 5 is a schematic perspective close-up view of one embodiment of a distal end portion of the lead introducer of FIG. 4, according to the invention.

FIG. 5 is a schematic perspective close-up view of one embodiment of a distal end portion of the lead introducer 302. In at least some embodiments, the inner needle 310, the outer needle 330, and the splittable member 350 are coupleable to one another such that the distal end portions 316 and 336 of the inner needle 310 and the outer needle 330, respectively, extend distally beyond the distal end portion 356 of the splittable member 350.

In at least some embodiments, the stylet 370 is coupleable to the inner needle 310, the outer needle 330, and the splittable member 350 such that the distal end portion 376 of the stylet 370 also extends distally beyond the distal end portion 356 of the splittable member 350. In FIG. 5, the distal end portion of the stylet 370 is shown disposed in a lumen 526 defined along the longitudinal length 338 of the inner needle 310.

The distal tip sections 322 and 342 of the inner needle 310 and the outer needle 330, respectively, may have slanted faces with sharpened ends suitable for piercing patient tissue during insertion of the lead introducer 302 into the patient. In at least some embodiments, the slanted faces of the distal tip sections 322 and 342 of the inner needle 310 and the outer needle 330, respectively, are ground down with the inner needle 310 nested with the outer needle 330 to form a matched set. In embodiments of the lead introducer that include the stylet, the stylet may also be ground down with the stylet nested within the inner needle 310 and the outer needle 330 to form a matched set.

Figure 6A:
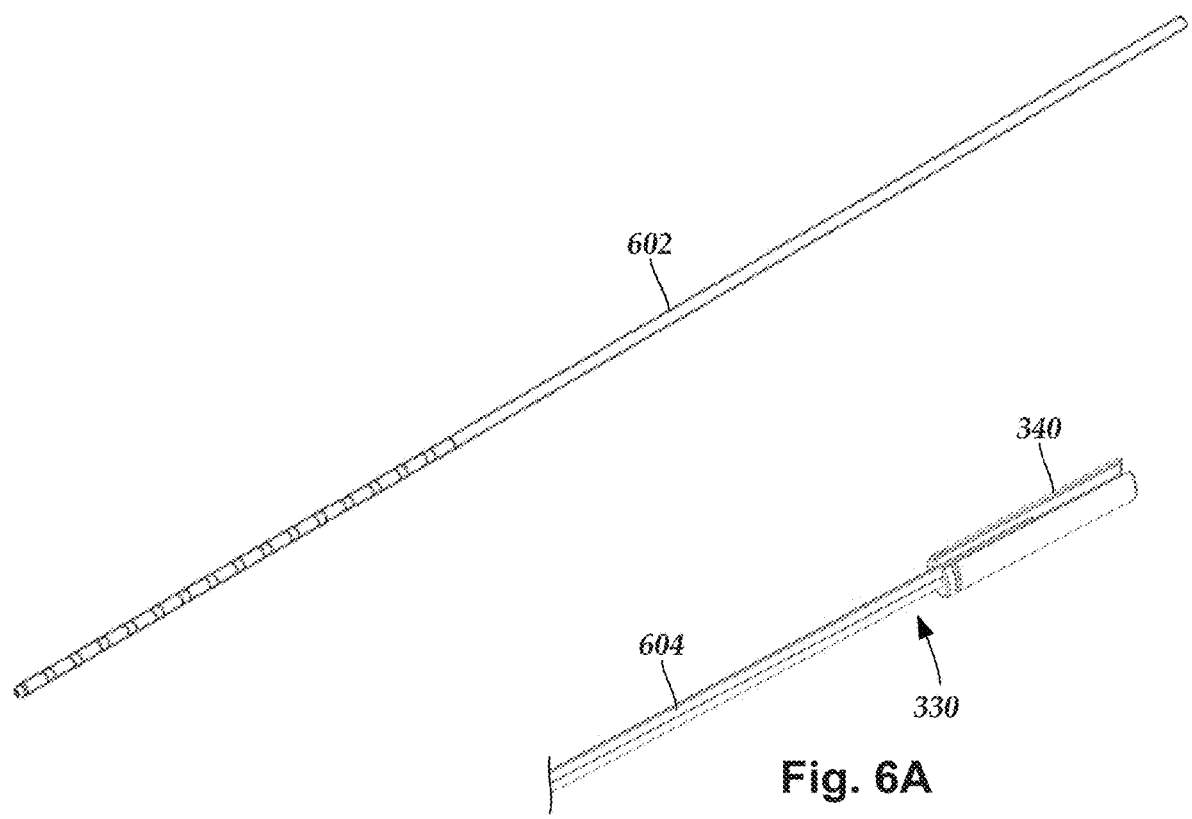
FIG. 6A is a schematic perspective view of one embodiment of a distal end portion of a lead and a portion of an outer needle of the lead introducer of FIG. 3, the outer needle defining an open channel extending along a length of the outer needle, the open channel suitable for receiving the lead, according to the invention.
Figure 6B:
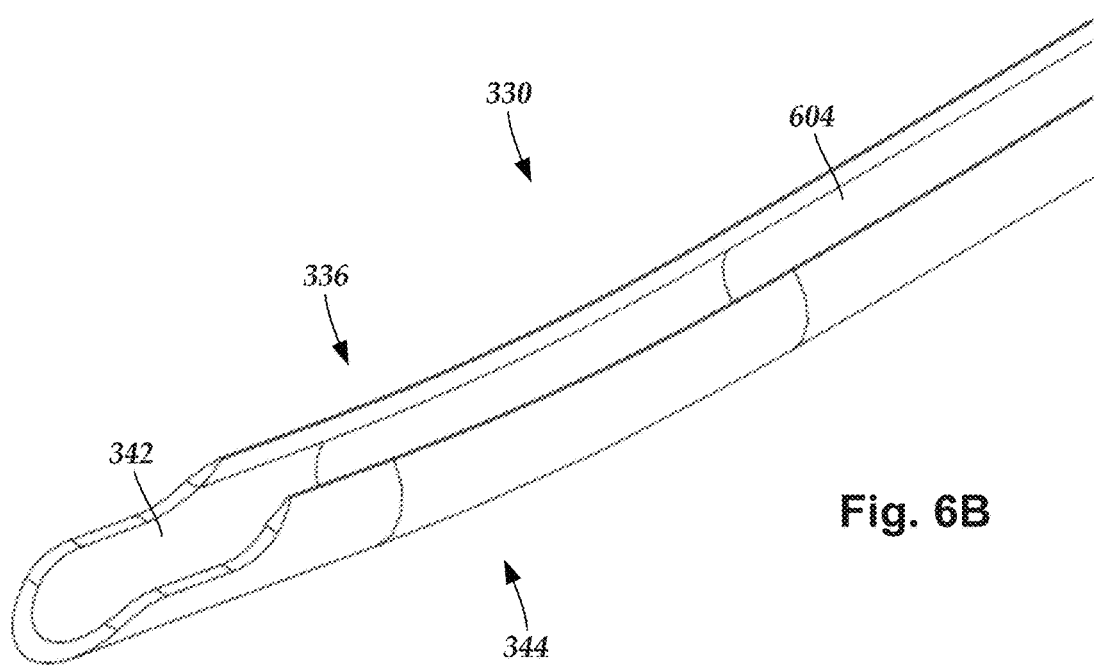
FIG. 6B is a schematic perspective view of one embodiment of a distal end portion of the outer needle of FIG. 6A, according to the invention.

Turning to FIGS. 6A-6B, the outer needle is designed to sequentially receive the inner needle and a lead during a lead-implantation procedure. The inner needle and the lead are received by an open channel extending along the longitudinal length of the outer needle.

FIG. 6A illustrates, in perspective view, one embodiment of a distal end portion of a lead and a portion of the outer needle 330. An open channel 604 is defined along the longitudinal length of the outer needle 330. As shown in FIG. 6A, the open channel 604 also extends along an entire length of the proximal hub 340 of the outer needle 330.

In some embodiments, the lead has an isodiametric lead body. In other embodiments, the lead has a non-isodiametric lead body. In at least some embodiments, the lead includes one or more elements (e.g., a junction, adaptor, or the like) disposed along the length of the lead which has a transverse cross-sectional shape or size that is different from the distal end portion of the lead. In at least some embodiments, the distal end portion of the lead has a transverse cross-sectional shape that is similar to a cross-sectional shape of the inner needle 310. In at least some embodiments, the one or more elements of the lead having a different transverse cross-sectional shape or size from the distal end portion of the lead are disposed along a proximal end portion of the lead.

In at least some embodiments, the inner needle 310 is shaped such that the inner needle 310 does not separate laterally from the open channel 604 when the inner needle 310 is received by the outer needle 330. In alternate embodiments, the inner needle 310 is free to separate laterally from the open channel 604 of the outer needle 330 when the inner needle 310 is received by the outer needle 330. In at least some embodiments, the inner needle 310 is insertable into, and removable from, the open channel 604 of the outer needle 330 solely by sliding the inner needle 310 axially along the open channel 604. In at least some embodiments, the inner needle 310 is configured and arranged to at least substantially fill the open channel 604 when the inner needle 310 is disposed in the open channel 604.

The open channel 604 is configured and arranged to receive the lead when the inner needle 310 is not disposed in the open channel 604. In at least some embodiments, the lead is free to separate laterally from the open channel 604 of the outer needle 330 when the inner needle 310 is received by the outer needle 330. In at least some embodiments, the lead is insertable into, and removable from, the open channel 604 of the outer needle 330 by sliding the lead axially along the open channel 604.

In at least some embodiments, the open channel 604 is configured and arranged to receive the lead such that the lead is separatable from the open channel 604 without moving the lead axially relative to the outer needle 330. In at least some embodiments, the open channel 604 has a width that is no less than a maximum diameter of the lead.

In at least some embodiments, the lead has a diameter that is larger than the space between the two opposing edges of the open channel 604 of the outer needle 330. In which case, the lead typically does not pass laterally through the open channel 604 due solely to the force of gravity. The body of the lead is typically formed from a deformable material. In at least some embodiments, the lead is removable from the open channel 604 by applying enough lateral force to at least one of the lead or the outer needle 330 to deform the lead enough to enable the lead to be passed laterally out through the open channel 604.

The open channel 604 can have any transverse cross-sectional shape suitable for sequentially retaining the inner needle 310 and the lead. In at least some embodiments, the open channel 604 has a transverse cross-sectional shape that is U-shaped. Alternately, the open channel 604 can have a transverse cross-section that is horseshoe-shaped, C-shaped, or the like.

Figure 6C:
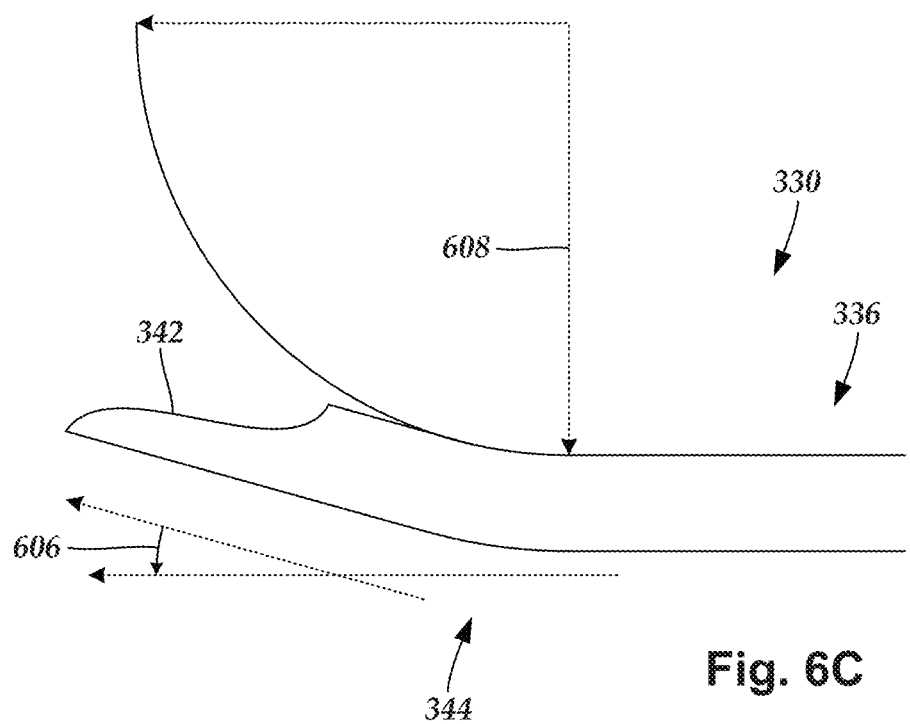
FIG. 6C is a schematic side view of one embodiment of a distal end portion of the outer needle of FIG. 6A, according to the invention.

FIG. 6B illustrates, in perspective view, one embodiment of the distal end portion 336 of the outer needle 330. FIG. 6C illustrates, in side view, one embodiment of the distal end portion 336 of the outer needle 330. The optional bend 344 is formed along the distal end portion 336 of the outer needle 330. In at least some embodiments, the bend 344 is formed with the open channel 604 extending along the concave portion of the bend 344.

In at least some embodiments, the bend 344 has an angle 606 that is at least 5°, 10°, 15°, or 20°. In at least some embodiments, the bend 344 has an angle 606 that is no greater than 20°, 15°, or 10°. In at least some embodiments, the bend 344 has an angle 606 that is at least 5° and no greater than 20°. In at least some embodiments, the bend 344 has an angle 606 that is at least 10° and no greater than 15°.

In at least some embodiments, the outer needle 330 is rigid. In at least some embodiments, the outer needle 330 is designed so that the bend 344 maintains a particular shape throughout a lead-implantation procedure. The outer needle 330 can have any suitable bend radius 608 (i.e., the minimum radius that the outer needle 330 can be bent without kinking). In at least some embodiments, the outer needle 330 has a bend radius 608 of at least 0.25 inches (0.6 cm), 0.5 inches (1.3 cm), 0.75 inches (1.9 cm), 1 inch (2.5 cm), 1.25 inches (3.2 cm), 1.5 inches (3.8 cm), or 1.75 inches (4.4 cm). In at least some embodiments, the outer needle 330 has a bend radius 608 that is no greater than 2 inches (5.1 cm), 1.75 inches (4.4 cm), 1.5 inches (3.8 cm), 1.25 inches (3.2 cm), 1 inch (2.5 cm), 0.75 inches (1.9 cm), or 0.5 inches (1.3 cm). In at least some embodiments, the outer needle 330 has a bend radius 608 that is at least 0.25 inches (0.6 cm) and no greater than 2 inches (5.1 cm).

The outer needle 330 is formed from a rigid material suitable for patient insertion, such as stainless steel. In at least some embodiments, the body 332 of the outer needle 330 is straight (or substantially straight) except for along the bend 344. The outer needle 330 can be formed in any suitable manner including, for example, shape extrusion/drawing, fabricating from a hypodermic needle tubing and forming the open channel via electrical discharge machining (e.g., wire or sinker), slot milling, or the like. The body 332 of the outer needle 330 can be attached to the proximal hub 340 in any suitable manner including, for example, laser welding. In at least some embodiments, the lateral circumference of the outer needle 330 is no greater than sixteen gauge, fifteen gauge, fourteen gauge, thirteen gauge, twelve gauge, eleven gauge, ten gauge, nine gauge, or eight gauge.

The inner needle 310 is formed from a material that is sufficiently flexible to be insertable across the bend 344 of the outer needle 330 when the inner needle 310 is extended along the open channel 604 of the outer needle 330. The inner needle 310 is also sufficiently flexible to be removed from the open channel 604 when the outer needle 330 is received by the splittable member 350. The inner needle 310 is also rigid enough to be insertable through the open channel 604 of the outer needle 330, either with or without the aid of the stylet 370 inserted into the lumen 526 of the inner needle 310.

The inner needle 310 is formed from any suitable material including, for example, a flexible plastic resin (e.g., nylon, polyester, polyurethane, or the like), or the like. Alternately, the inner needle 310 can be formed from stainless steel or other metal. In at least some embodiments, the inner needle 310 is formed from the same material as the outer needle 330. In at least some embodiments, the inner needle 310 is formed from a material that is more flexible than the outer needle 330. In at least some embodiments, the outer needle 330 is formed from a material that is more rigid than the splittable member 350. In at least some embodiments, the outer needle 330 is formed from a material that is rigid enough to enable the outer needle 330 to be used to guide (e.g., enable lateral steering) the splittable member 350 within a patient when the outer needle 330 is disposed in the splittable member 350. In at least some embodiments, for curved distal tip outer needles (see, FIGS. 6B and 6C), the inner needle could be made from a rigid metal such as stainless steel and incorporate partial circumferential laser cuts at the distal end of the inner needle to allow the distal end of the inner needle to conform with the bend in the outer needle during insertion and withdrawal.

Figure 7A:
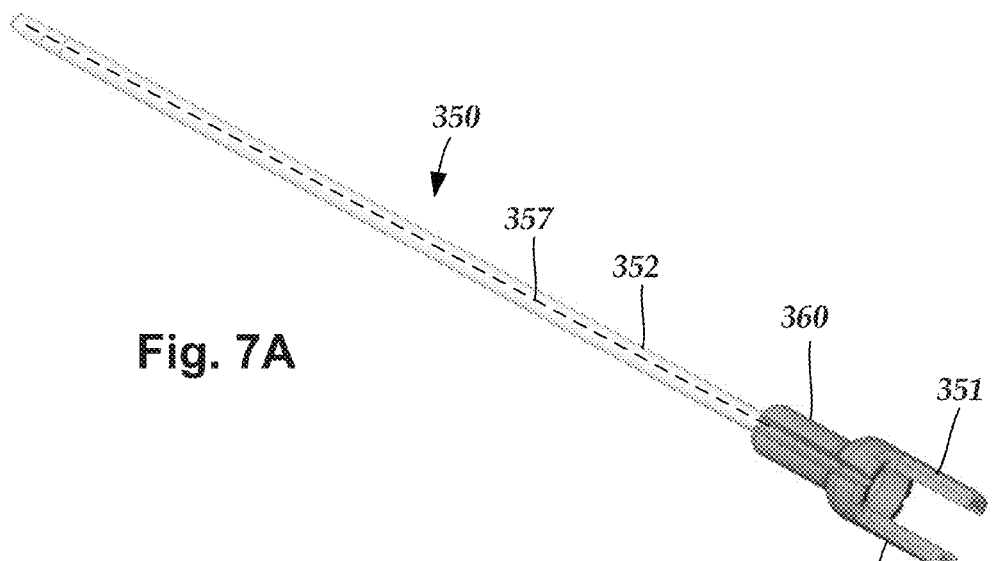
FIG. 7A is a schematic perspective view of one embodiment of a splittable member of the lead introducer of FIG. 4, according to the invention.
Figure 7B:
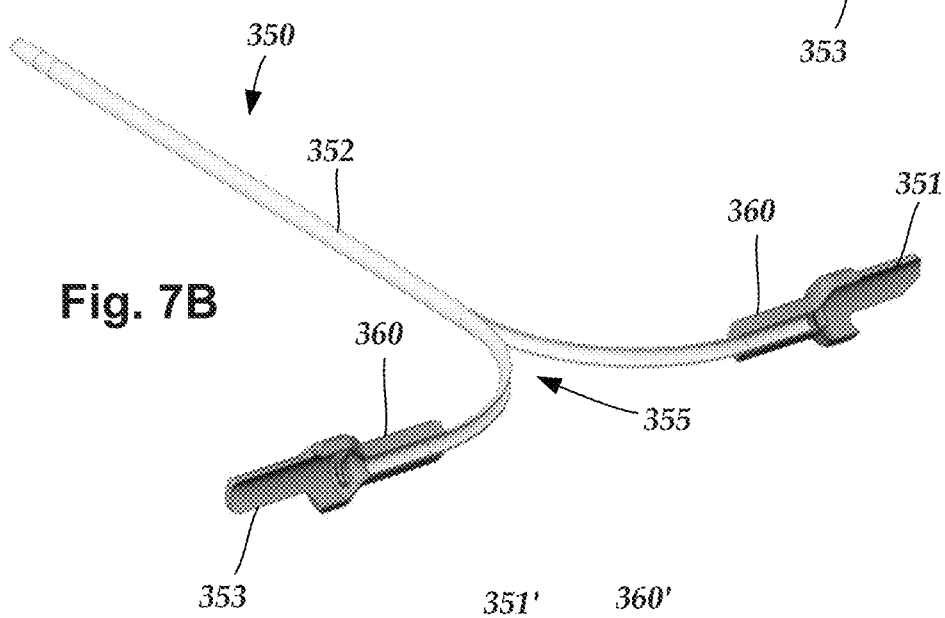
FIG. 7B is a schematic perspective view of the splittable member of FIG. 7A that is partially split, according to the invention.
Figure 7C:
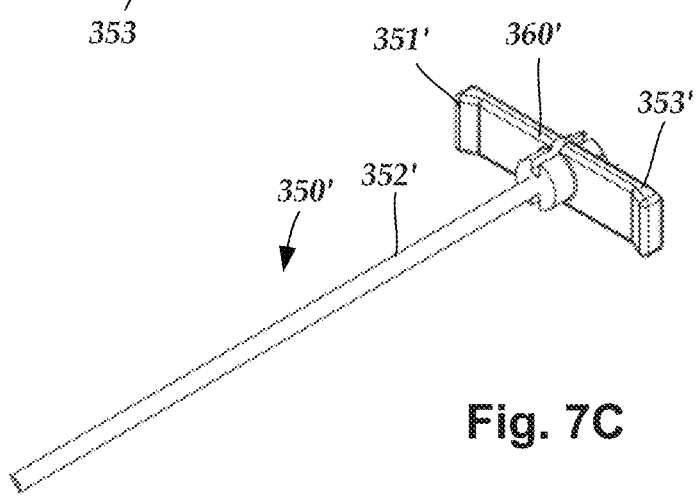
FIG. 7C is a schematic perspective view of another embodiment of a splittable member of the lead introducer of FIG. 4, according to the invention.

FIGS. 7A and 7B illustrate one embodiment of the splittable member 350 with a body 352 and a hub 360. The hub 360 includes two pull-apart tabs 351, 353 that extend proximally away from the splittable member body 352 and parallel to a longitudinal axis of the splittable member. FIG. 7B is a schematic perspective view of one embodiment of the splittable member 350 being split apart to remove the splittable member 350 from a lead. The splittable member 350 defines a lumen 355 into which the inner needle, outer needle, or a lead can be inserted. FIG. 7C illustrates an alternative splittable member 350' with hub 360' having pull-apart tabs 351', 353' that extend laterally away from the splittable member body 352'.

The longitudinally extending pull-apart tabs 351, 353 in the embodiment of FIGS. 7A and 7B may be desirable as the tabs do not extend substantially laterally away from the remainder of the splittable member 350 and are, therefore, less likely to be in the way during a surgical procedure. Moreover, as described below, other portions of the arrangement such as the hub of the inner or outer needle can include a fixture to hold the pull-apart tabs together and, thereby, avoid or reduce the likelihood that the pull-apart tabs will be inadvertently separated (potentially causing the splittable member to partially or fully split) until the practitioner decides to do so. In contrast, the pull-apart tabs 351', 353' in the embodiment of FIG. 7C may be easier to grasp and pull apart when the practitioner desires to do so. Although the remainder of the illustrated embodiments incorporate the pull-apart tab arrangement illustrated in FIGS. 7A and 7B, it will be understood that such embodiments can also be modified to include the pull-apart tab arrangement illustrated in FIG. 7C.

In at least some embodiments, the splittable member 350 includes one or more perforated (or scored, weakened, thinned, or the like) regions 357 extending along at least a portion of the longitudinal length 358 of the splittable member 350 from between the at least two pull-apart tabs 351, 353. In at least some embodiments, when the at least two pull-apart tabs 351, 353 are separated from one another, for example, by pulling each pull-apart tab laterally (i.e., away from the other pull-apart tab(s) in directions approximately orthogonal to the splittable member 350), the splittable member 350 separates along the one or more perforated (or scored, weakened, thinned, or the like) regions 357.

In other embodiments, the splittable member 350 can be pre-split, perforated, scored, weakened, or thinned only within the splittable member hub 360 and have no further perforations or the like along the length of the splittable member. Materials, such as polytetrafluoroethylene (PTFE), when extruded can split easily and reliably in the direction of the extrusion without having to pre-score or perforate.

Figure 8A:
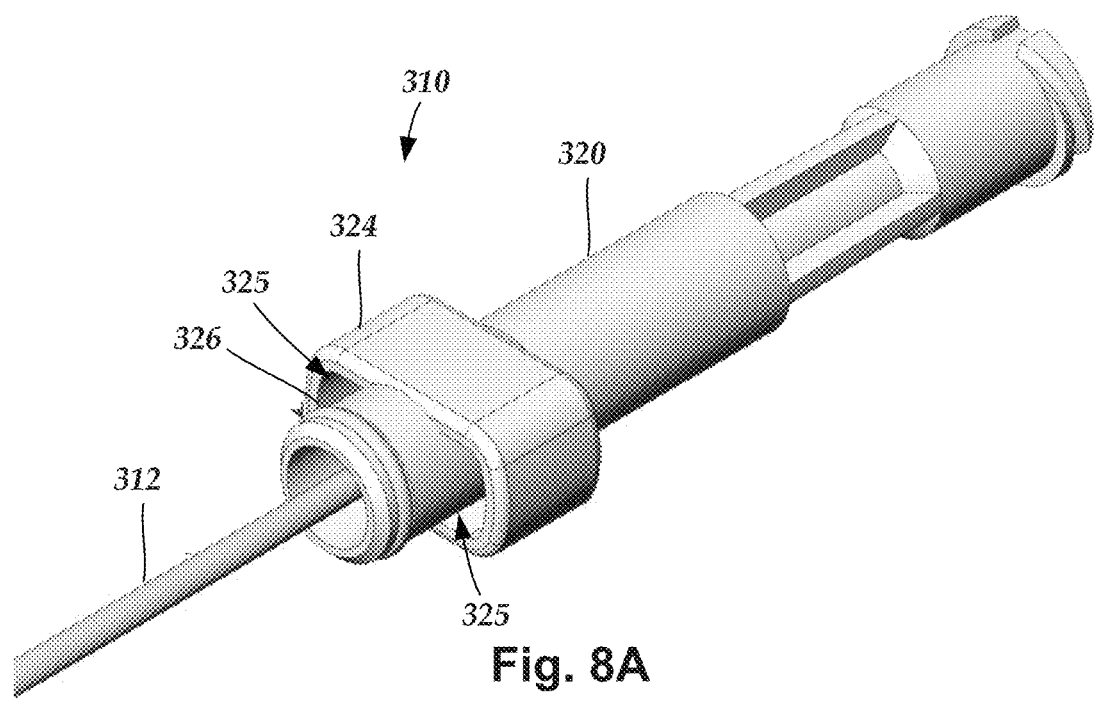
FIG. 8A is a schematic perspective view of one embodiment of a proximal end portion of an inner needle of the lead introducer of FIG. 4, according to the invention.
Figure 8B:
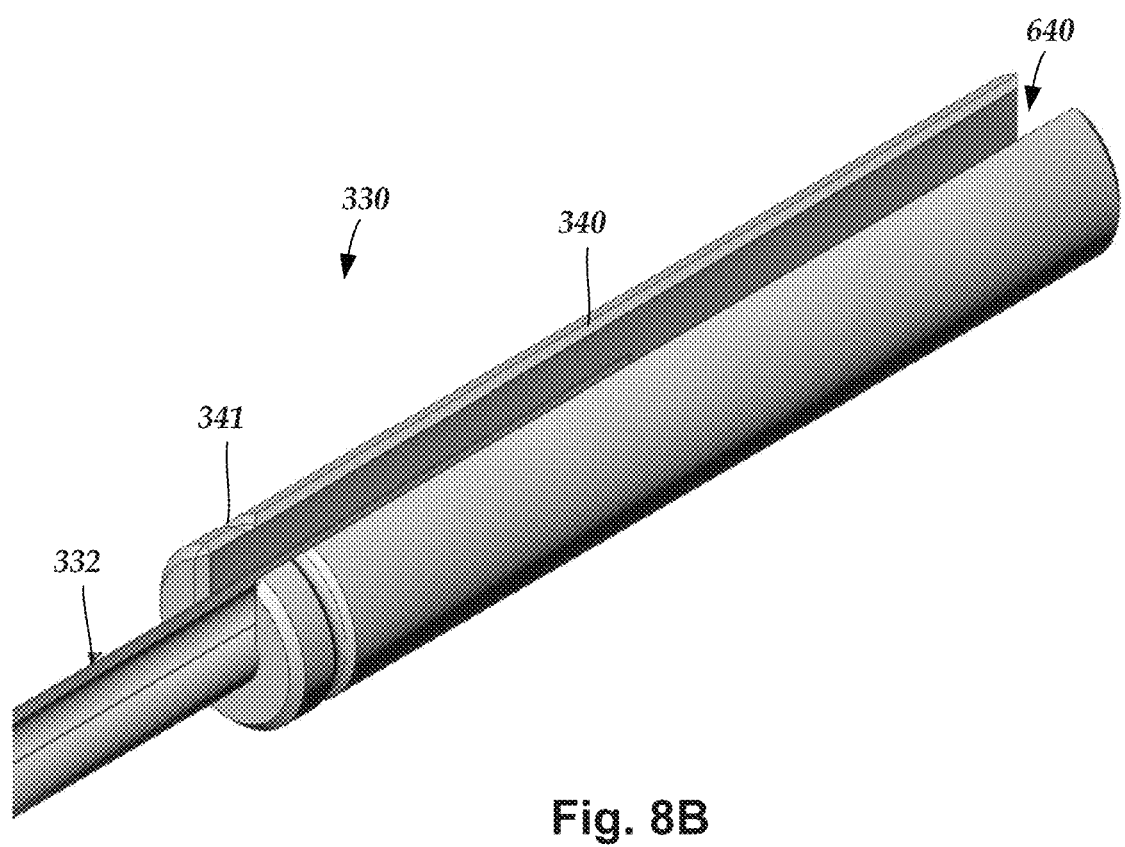
FIG. 8B is a schematic perspective view of one embodiment of a proximal end portion of an outer needle of the lead introducer of FIG. 4, according to the invention.
Figure 8C:
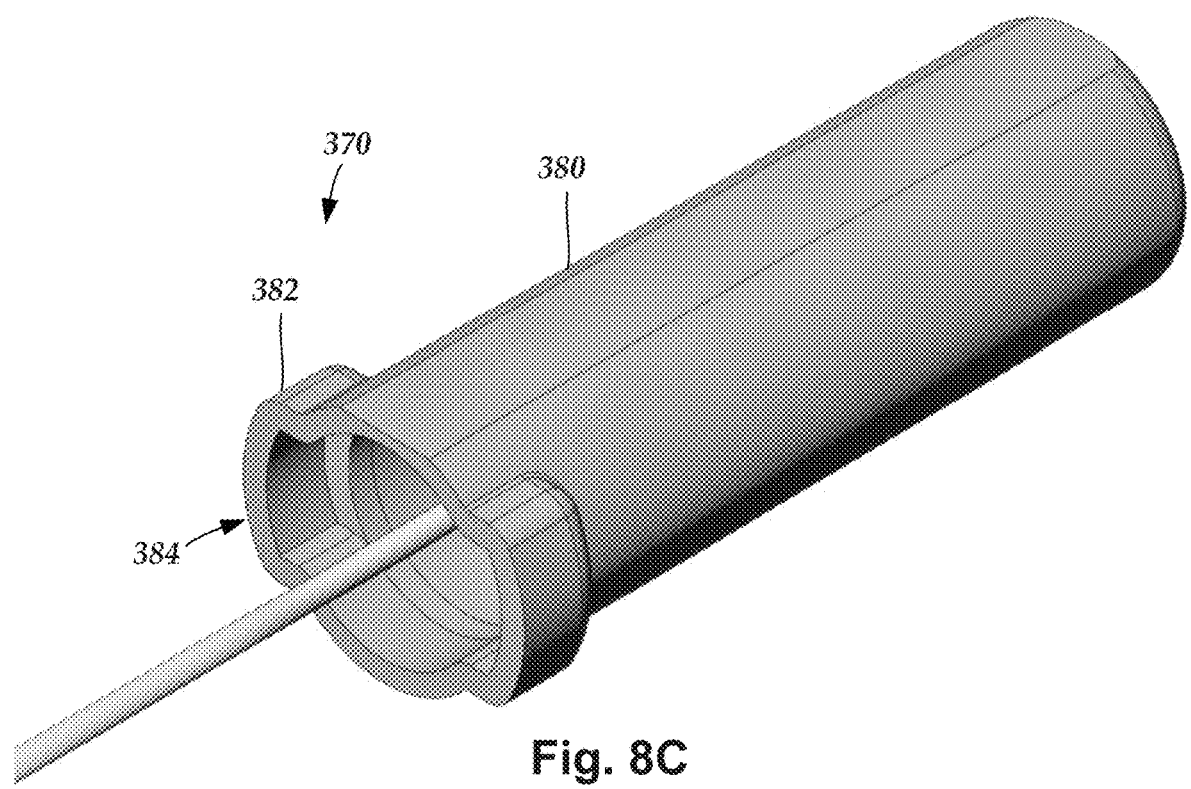
FIG. 8C is a schematic perspective view of one embodiment of a distal end portion of a stylet of the lead introducer of FIG. 4, according to the invention.
Figure 8D:
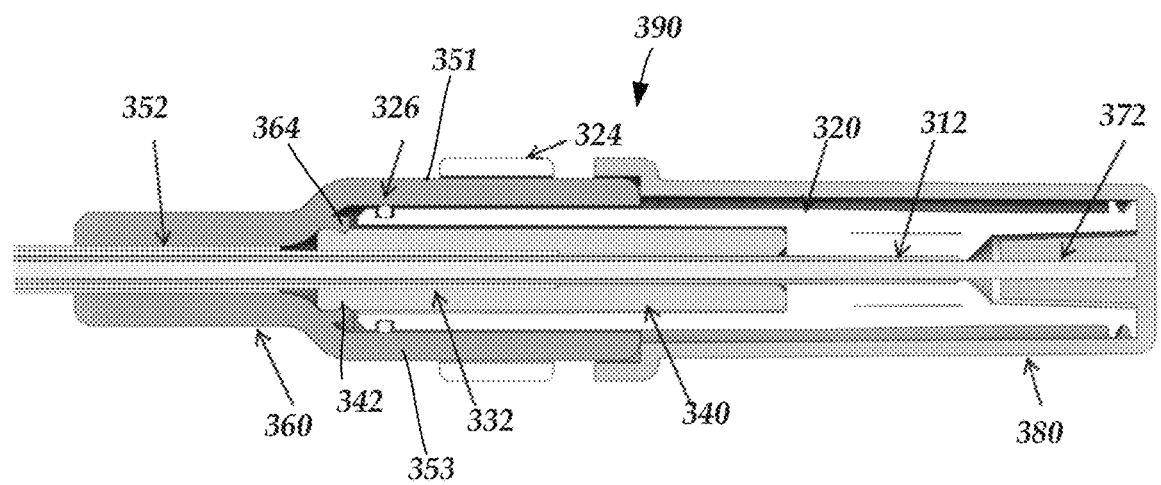
FIG. 8D is a longitudinal cross-sectional view of one embodiment of a distal end of the lead introducer of FIG. 4 showing the nested arrangement of the splittable member hub, inner needle hub, outer needle hub, and stylet hub, according to the invention.

FIG. 8A illustrates one embodiment of the proximal portion of the inner needle 310 with the inner needle hub 320. FIG. 8B illustrates one embodiment of the proximal portion of the outer needle 330 with the outer needle hub 340. FIG. 8C illustrates one embodiment of the proximal portion of the stylet 370 with the stylet hub 380. FIG. 8D is a cross-sectional illustration of the nested arrangement of the inner needle hub 320, outer needle hub 340, splittable member hub 360, and stylet hub 380. Also illustrated are the stylet body 372, inner needle body 312, outer needle body 332, and splittable member body 352. As illustrated, the outer needle hub 340 is inserted into the splittable member hub 360 with a distal portion remaining outside the splittable member hub. The inner needle hub 320 fits over the outer needle hub 340 with a proximal portion received within the splittable member hub 360. The stylet hub 380 fits over the inner needle hub 320.

Figure 9:
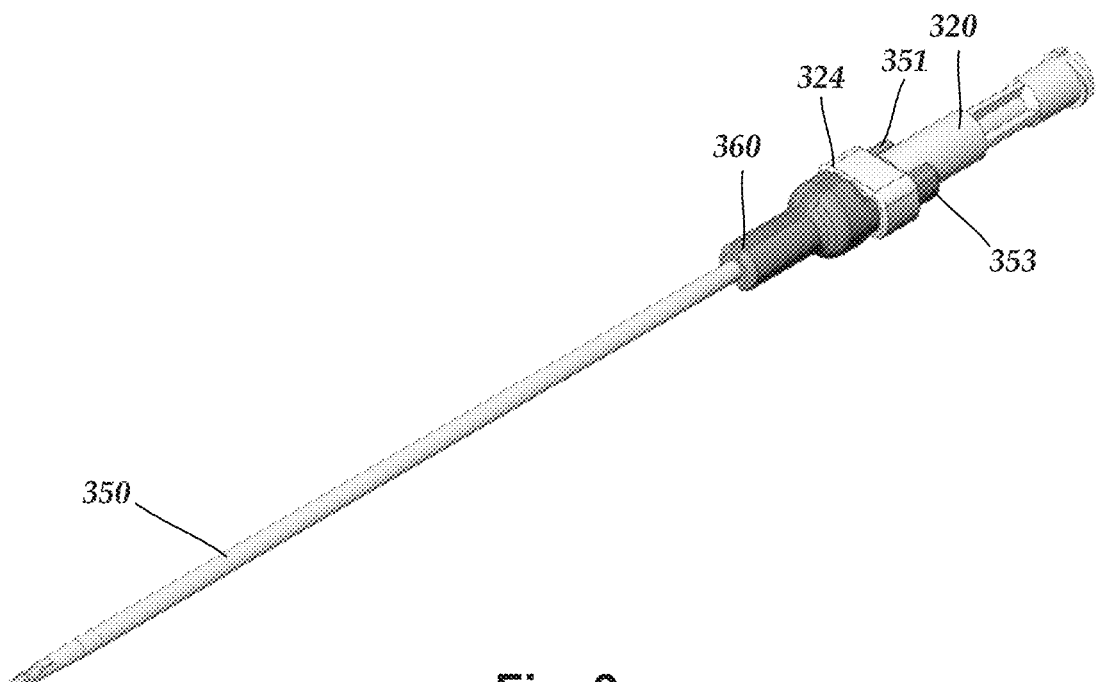
FIG. 9 is a schematic perspective view of the lead introducer of FIG. 4 without the stylet, according to the invention.

Returning to FIG. 8A, in at least some embodiments, the inner needle hub 320 includes a collar 324 which defines two openings 325. In at least some embodiments, the openings 325 are formed between the collar 324 and another portion of the inner needle hub 320, as illustrated in FIG. 8A. These openings 325 are arranged to receive the pull-apart tabs 351, 353 of the splittable member 350 of FIGS. 7A and 7B. This arrangement is illustrated in cross-section in FIG. 8D and in side view in FIG. 9. In at least some embodiments, the openings 325 can be open at both longitudinal ends to allow the pull-apart tabs 351, 353 to pass through the openings.

When the pull-apart tabs 351, 353 are received within the openings 325 of the collar 324 of inner needle hub 320, the pull-apart tabs cannot be easily pulled apart, thereby avoiding or reducing the likelihood of the pull-apart tabs being inadvertently separated (and the splittable member 350 partially or fully split) during use. The inner needle 310 is typically removed and replaced by a lead prior to splitting the splittable member 350.

In at least some embodiments, the inner needle hub 320 includes an annular seal member 326 disposed around a portion of the hub as illustrated in FIG. 8A. In the illustrated embodiment, the annular seal member 326 is a flexible O-ring, but it will be understood that any other suitable annular seal member can be used. In at least some embodiments, the annular seal member 326 is made of silicone or any other suitable flexible elastomeric material. The annular seal member 326 is arranged to fit against the interior surface of the splittable member hub 360 to form a seal between the splittable member hub and the inner needle hub 320, as illustrated in FIG. 8D. It has been found that in other arrangements fluid may be drawn from the distal tip between the splittable member and the outer needle or between the inner and outer needle, particularly if the inner and outer needles are relaxed or pulled back, causing leakage. The annular seal member 326 in contact with the splittable member hub 350, prevents or reduces the leakage of fluid between the splittable member hub and the inner needle hub.

Turning to FIG. 8B, the outer needle hub 340 includes a continuation of the open channel 640 described above. In at least some embodiment, the outer needle hub also includes a detent 341. In these embodiments, the splittable member hub 350 preferably includes a ridged structure 364 that forms a friction fit or snap fit with the detent 341 of the outer needle hub 340, as illustrated in FIG. 8D. The detent/ridged structure arrangement can facilitate retention of the outer needle within the splittable member when the inner needle is removed from the outer needle. The ridged structure 364 is preferably removable from contact with the detent 341 when the practitioner grips the outer needle hub 340 and pulls it away from the splittable member hub 360. In other embodiments, the distal tip of the outer needle hub 340 and the inside bore of the splittable member hub 350 can be arranged to form a press-fit (interference fit) that stabilized and retains outer needle within the splittable member when the inner needle is removed from the outer needle.

Figure 10:
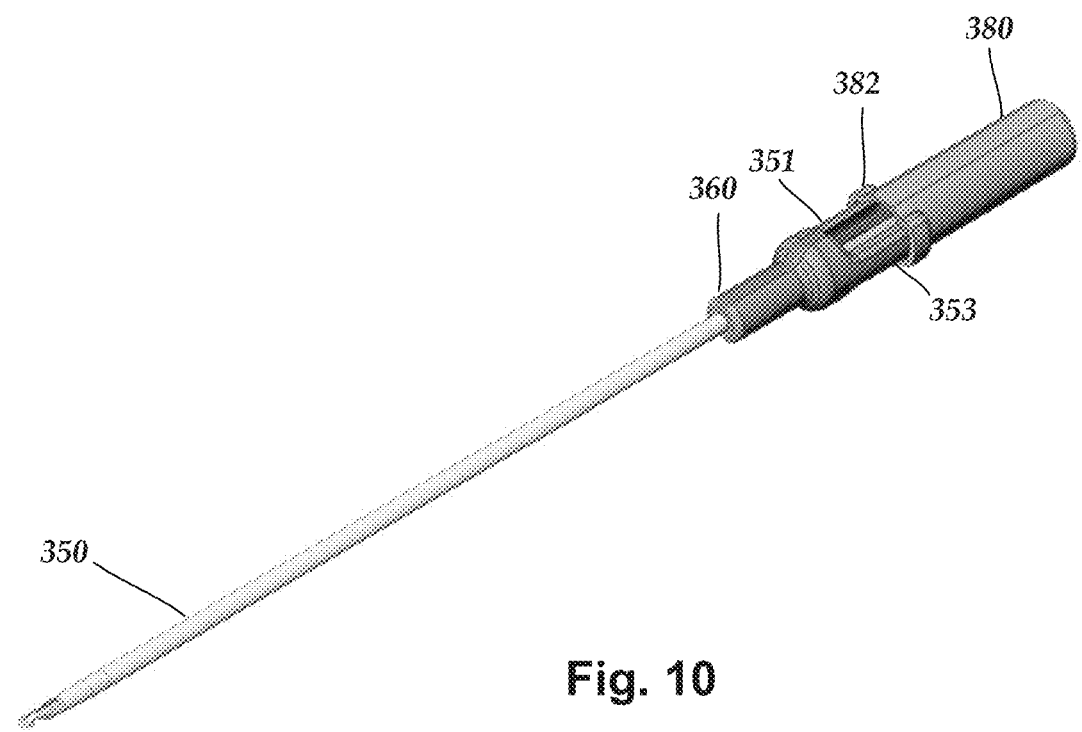
FIG. 10 is a schematic perspective view of the lead introducer of FIG. 4 without the inner needle, but with the stylet inserted, according to the invention.

Turning to FIG. 8C, in at least some embodiments, the stylet hub 380 includes projections 382 that define cavities 384 that can receive the tips of the pull-apart tabs 351, 353 of the splittable member hub 360. When engaged, the cavities 384 can prevent or reduce the likelihood of the pull-apart tabs being inadvertently separated (and the splittable member 350 partially or fully split) during use of the stylet. In addition, the pull-apart tabs 351, 353 can also act as an insertion stop for the stylet 370 to prevent the distal end of the stylet from protruding out of the distal tip of the outer needle if the inner needle is omitted from the assembly. This could happen, absent the pull-apart tabs, if the inner needle is inadvertently absent when the stylet is inserted into the outer needle and splittable member combination. FIG. 10, however, illustrates that the pull-apart tabs 351, 353 stop further insertion of the stylet 370, even in the absence of the inner needle, when the pull-apart tabs are received in the cavities 384 defined by the projections 382 of the stylet hub 380. Thus, this arrangement provides an additional safety feature.

Figure 11A:
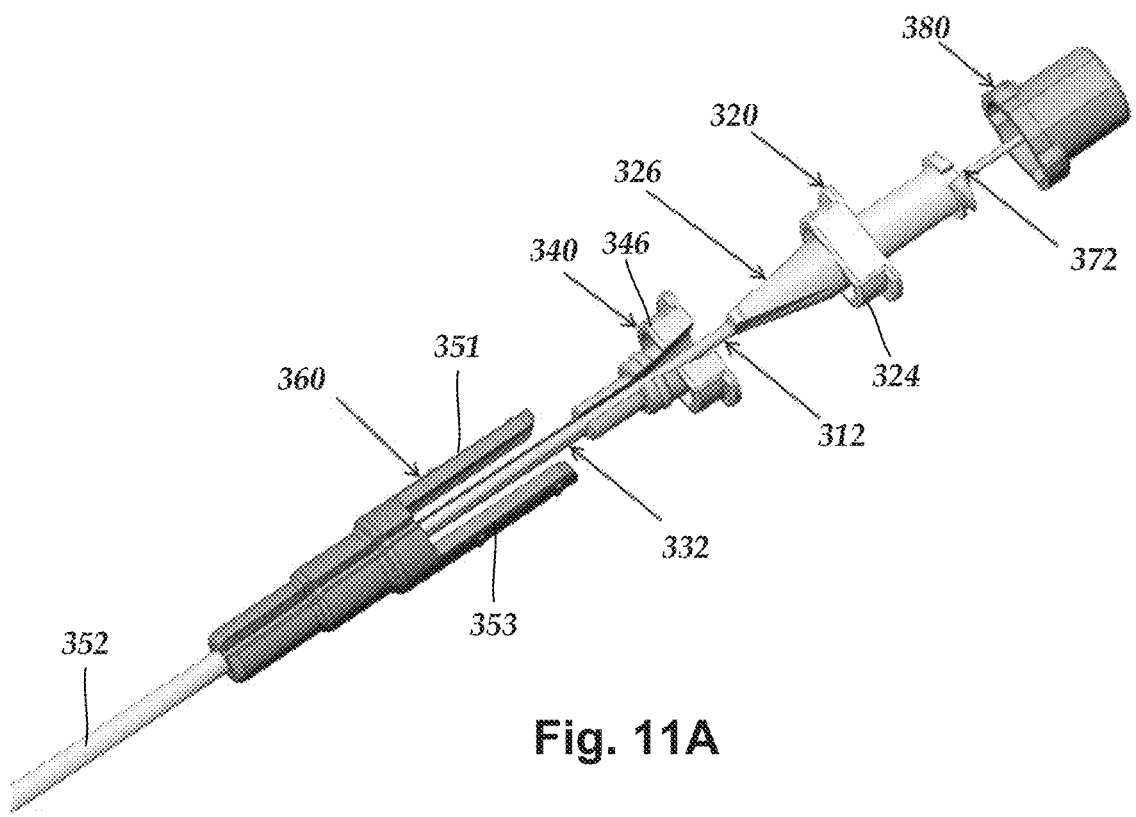
FIG. 11A is a schematic perspective exploded view of another embodiment of a lead introducer configured and arranged for facilitating implantation of a lead of an electrical stimulation system into a patient, the lead introducer including a multi-piece insertion needle, a splittable member, and an optional stylet, according to the invention.
Figure 11B:
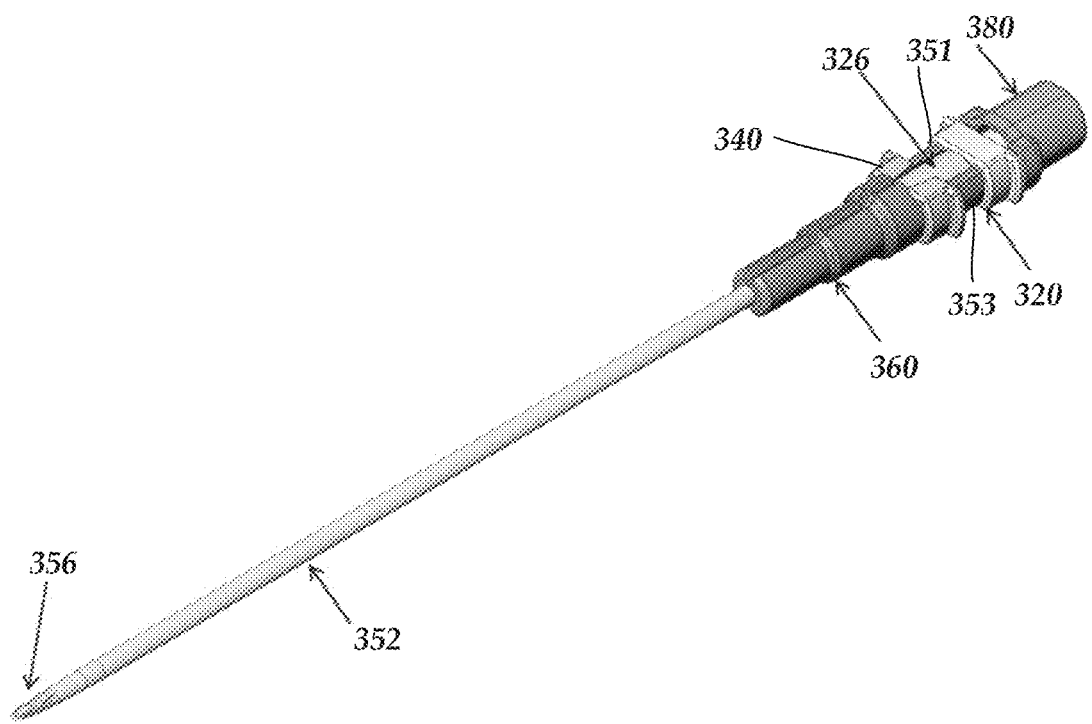
FIG. 11B is a schematic perspective view of one embodiment of the lead introducer of FIG. 11A with the multi-piece insertion needle and stylet nested in the splittable member of the lead introducer, according to the invention.
Figure 11C:
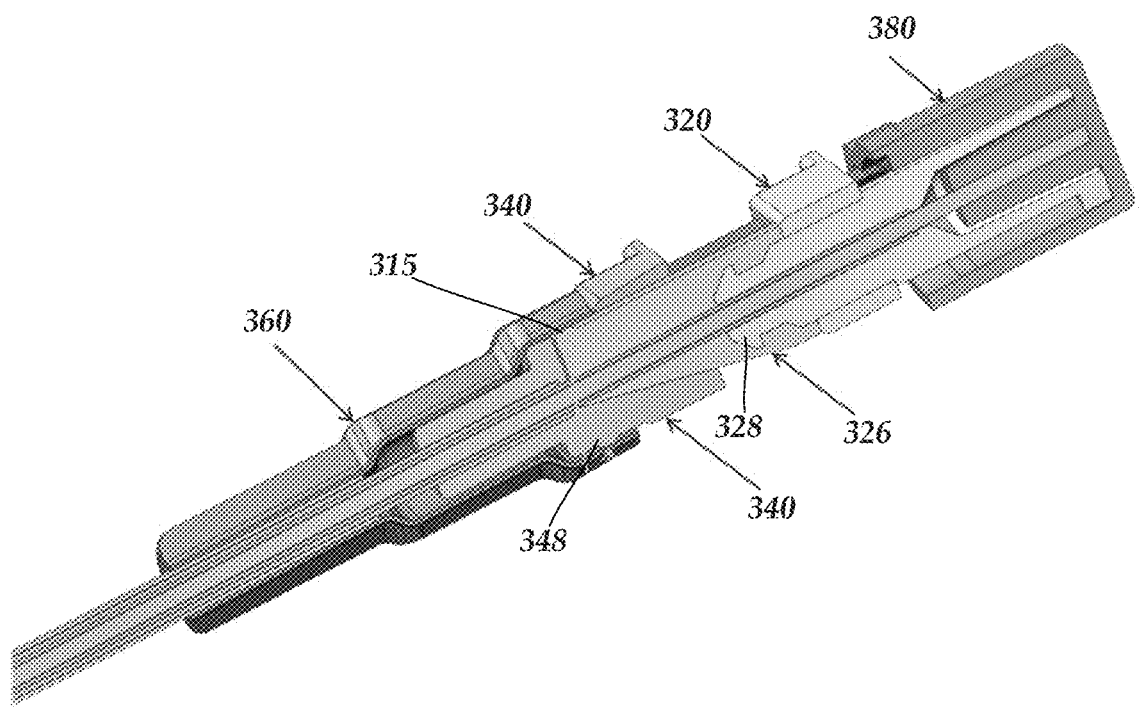
FIG. 11C is a longitudinal cross-sectional view of one embodiment of a distal end of the lead introducer of FIG. 11A showing the nested arrangement of the splittable member hub, inner needle hub, outer needle hub, and stylet hub, according to the invention.
Figure 11D:
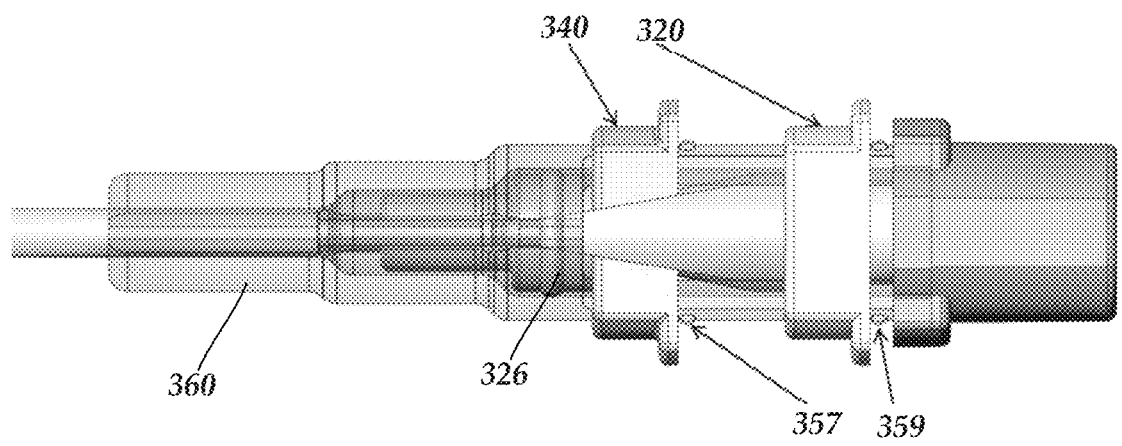
FIG. 11D is a schematic side view of one embodiment of a distal end of the lead introducer of FIG. 11A, according to the invention.
Figure 11E:
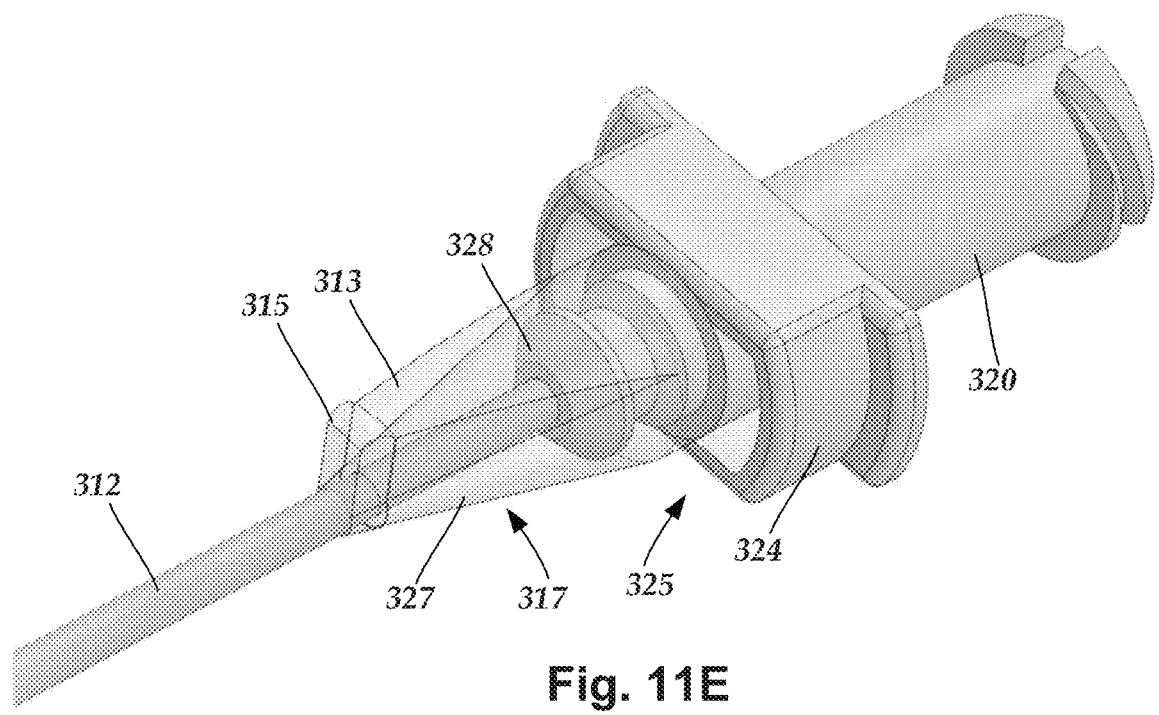
FIG. 11E is a schematic perspective view of one embodiment of a distal end portion of an inner needle of the lead introducer of FIG. 11A, according to the invention.
Figure 11F:
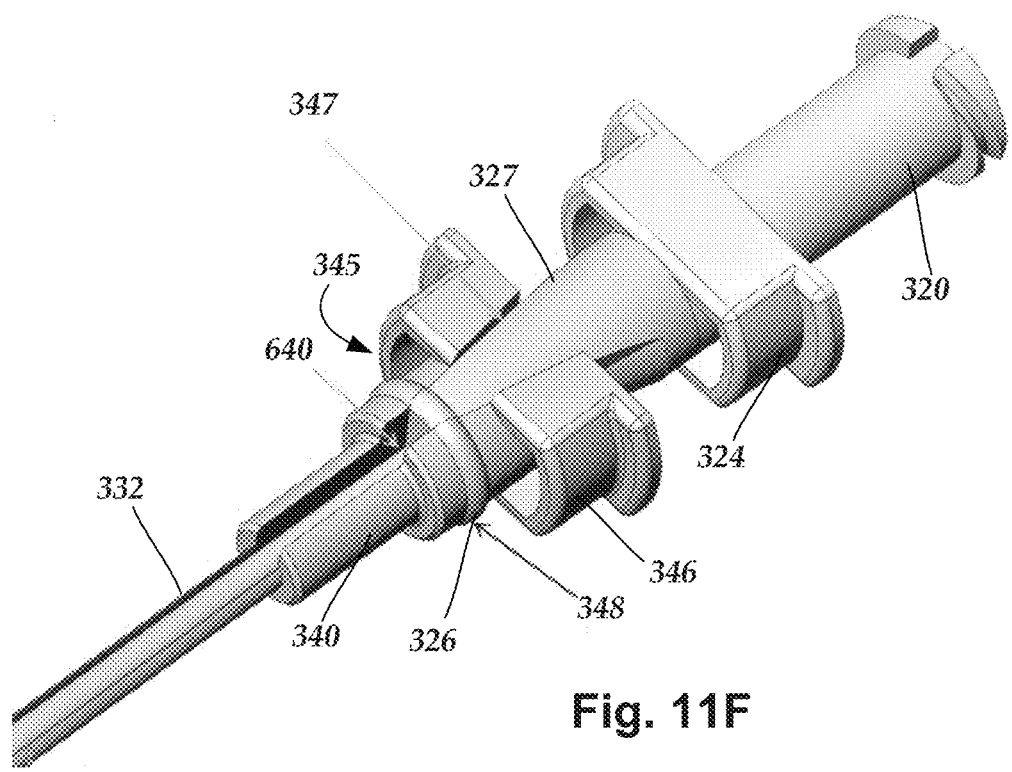
FIG. 11F is a schematic perspective view of one embodiment of a distal end portion of an inner needle and an outer needle of the lead introducer of FIG. 11A, according to the invention.

FIGS. 11A-11F illustrate another embodiment of lead introducer which is similar to the introducer illustrated in FIGS. 7A-10 except as discussed below. In particular, a seal element 327 of this embodiment, as best illustrated in FIGS. 11E and 11F, has a conical shape 317 except for a wedge 313 on one side that interfaces with a mating wedge-shaped opening 347 on the outer needle hub 340. Optionally or additionally, the seal element 327 includes a partial seal rib 315 that mates with a seal rib 348 on the outer needle hub 340 to provide an annular seal member 326 that forms a seal with the inner surface of the splittable member hub 360, as illustrated in FIGS. 11C, 11D, and 11F.

FIG. 11E illustrates the proximal end of the inner needle member with the inner needle hub 320 and inner needle body 312. The inner needle hub 320 includes a collar 324 with openings 325, as described above, and a seal element 327. The seal element 327 has a generally conical shape 317 except for a wedge 313 that extends from one side. The seal element 327 can be attached to the remainder of the inner member hub 320 using a post 328 that the seal element can be fit onto and attached using any suitable mechanism such as, for example, adhesive, interference fit, friction fit, or the like or any combination thereof. Optionally or additionally, the seal element 327 includes a partial seal rib 315 at or near the distal end of the seal element 327 with the partial seal rib extending radially outward from an adjacent portion of the seal element 327.

The outer needle hub 340, best illustrated in FIG. 11F, includes a wedge-shaped opening 347 to receive the wedge-shaped rib 313 of the inner needle hub 320. The outer needle hub 340 also includes a seal rib 348 that cooperates with the partial seal rib 315 to form an annular seal member 326.

The outer needle hub 340 optionally includes a collar 346 which defines two openings 345, as illustrated in FIG. 11F. In at least some embodiments, the openings 345 are formed between the collar 346 and another portion of the outer needle hub 340, as illustrated in FIG. 11F. These openings 345 are arranged to receive the pull-apart tabs 351, 353 of the splittable member 350 (see, for example, FIGS. 11A and 11B). In at least some embodiments, the openings 345 can be open at both longitudinal ends to allow the pull-apart tabs 351, 353 to pass through the openings.

When the pull-apart tabs 351, 353 are received within the openings 345 of the collar 346 of outer needle hub 340, the pull-apart tabs cannot be easily pulled apart, thereby avoiding or reducing the likelihood of the pull-apart tabs being inadvertently separated (and the splittable member 350 partially or fully split) during use. The outer needle 330 is typically removed prior to splitting the splittable member 350. The inner needle hub 320 can also include a collar 324 with openings 325 that also receive the pull-apart tabs 351, 353, as illustrated in FIG. 11E.

The pull-apart tabs 351, 353 may also include retention features 357, 359, as illustrated in FIG. 11D, which resist removal of the outer needle hub 340 or inner needle hub 320, respectively, from the splittable member 350. These retention features 357, 359 prevent or reduce inadvertent removal of the outer needle hub 340 or inner needle hub 320, but do allow the user to pull the inner needle or outer needle from the splittable member when desired. The retention features 357, 359 can be, for example, a protruding partial ring, one or more protruding dots, or the like disposed on both or either of the pull-apart tabs 351, 353.

Figures 12A, 12B:
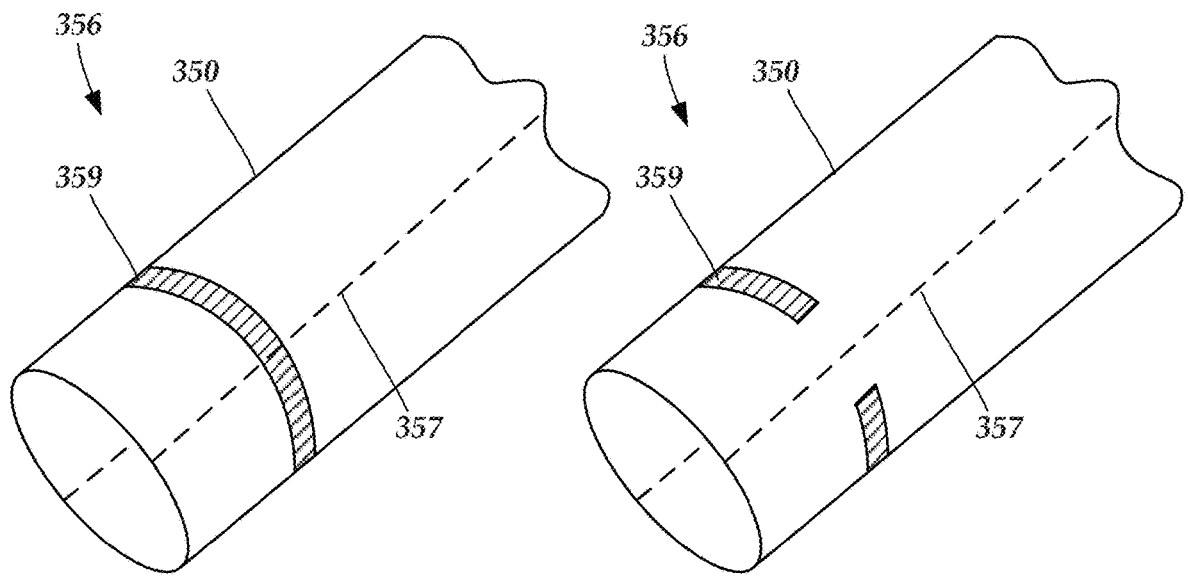
FIG. 12A is a schematic perspective view of one embodiment of a distal end of a splittable member with a radiopaque marking, according to the invention.
FIG. 12B is a schematic perspective view of a second embodiment of a distal end of a splittable member with a radiopaque marking, according to the invention.
Figure 12C:
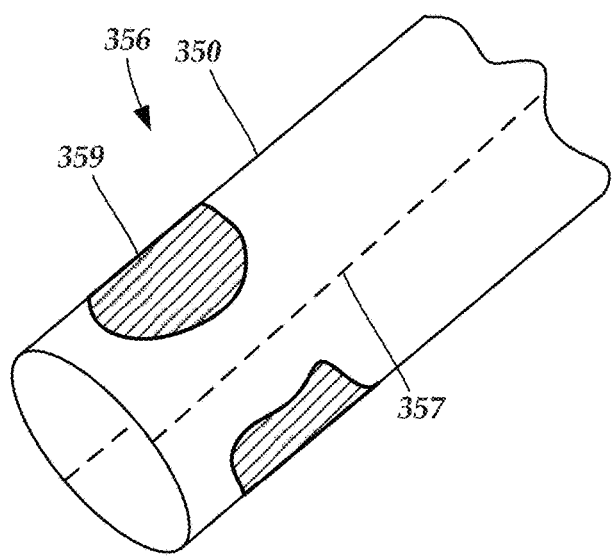
FIG. 12C is a schematic perspective view of a third embodiment of a distal end of a splittable member with a radiopaque marking, according to the invention.

In at least some embodiments, a radiopaque marker 359 can be provided at the distal end 356 of the splittable member 350, as illustrated in FIGS. 12A-12C. The radiopaque marker 359 can be useful for identifying the position of the splittable member during a surgical procedure. The radiopaque marker 359 can take any form including, but not limited to, a ring (FIG. 12A), partial ring features (FIG. 12B), or other shapes (FIG. 12C) which may extend over the perforated regions 357 (FIG. 12A) or are separated by the perforated regions 357 (FIGS. 12B and 12C).

One embodiment of a lead implantation procedure uses the lead introducer 302 to implant a lead at a target stimulation location. The inner needle 310 is inserted into the open channel 604 of the outer needle 330, and the outer needle 330 is inserted into the splittable member 350. In at least some embodiments, the stylet 370 is inserted into the lumen of the inner needle 310. It will be understood that, in some embodiments, the lead introducer 302 is pre-assembled during manufacture.

The assembled lead introducer 302 is inserted into a patient and guided in proximity to the target stimulation location (e.g., several vertebrae levels above or below the target stimulation location or a portion of the brain). In at least some embodiments, once the lead introducer 302 is in proximity to a target stimulation location fluid is introduced or removed through inner needle 310 to check for precise positioning of the lead introducer 302, for example, in an epidural space of the patient. In at least some embodiments, the stylet 370 is removed prior to introducing fluid into the patient via the lumen 526 of the inner needle 310.

Once the lead introducer 302 is positioned in the epidural space in proximity to the target stimulation location, the inner needle 310 may be removed and the distal end portion of the lead may be inserted into the open channel 604 of the outer needle 330 and the proximal opening of the sheath 350. Once the distal end portion of the lead is inserted into the open channel 604 of the outer needle 330, the distal end portion of the lead may be guided more closely to the target stimulation region. In at least some embodiments, the distal end portion of the lead is guided to the target stimulation region by the comparably rigid outer needle 330.

It may be advantageous to guide the lead within the patient while the lead is disposed in the outer needle 330 and the splittable member 350. The outer needle 330 and the splittable member 350 may provide the medical practitioner with the ability to steer the lead introducer 302 by applying a lateral force of the lead introducer 302 to direct the trajectory of the lead. When the outer needle 330 is removed from the lead prior to insertion, then the splittable member 350 may be too flexible to provide this steering ability. The outer needle 330 can also steer the lead by circumferentially rotating the outer needle 330 and the sheath 350, thereby adjusting the orientation of the distal bend 344 of the outer needle 330 (see, FIGS. 6B and 6C) within the epidural space or the curve at the distal needle bevel with a straight outer needle 330 (see FIG. 5). Such rotation directs the lead towards the right or the left as the lead exits the outer needle/sheath distal opening. In other embodiments, the practitioner may remove the outer needle and inner needle and guide the lead disposed within the splittable member using a lead stylet.

Once the distal end portion of the lead has been guided to the target stimulation location, the splittable member 350 and the outer needle 330 may be separated from the lead and removed from the patient. It will be understood that the splittable member 350 may be separated from the lead either before or after the outer needle 330 is separated from the lead. It will also be understood that the splittable member 350 may be removed from the patient either before or after the outer needle 330 is removed from the patient. In some embodiments, the outer needle 330 is separated from the lead prior to the splittable member 350 being separated from the lead. In other embodiments, the splittable member 350 is separated from the lead prior to the outer needle 330 being separated from the lead. In some embodiments, the outer needle 330 is removed from the patient prior to removal of the splittable member 350. In other embodiments, the splittable member 350 is removed from the patient prior to removal of the outer needle 330.

In at least some embodiments, the lead is guided to the target stimulation location while disposed in the outer needle 330 and the splittable member 350. The outer needle 330 is removed from the lead (and from the patient). The splittable member 350 is then split apart from the lead and removed from the patient.

In at least some embodiments, the splittable member 350 is separated into multiple longitudinal strips while pulling the splittable member 350 proximally along the lead. As the splittable member 350 splits apart, the distal end portion 356 of the splittable member 350 moves proximally along the lead, with an increasing amount of the lead extending through the distal end portion 356 of the splittable member 350. In at least some embodiments, an undersurface of the splittable member 350 includes a lubricious coating to facilitate the proximal movement of the splittable member 350.

Eventually, the splittable member 350 may be completely separated into two or more longitudinal strips, thereby separating completely from the lead and also from the patient. In at least some embodiments, the distal end portions of the splittable member 350 are extracted from the patient as the splittable member 350 is split apart. In at least some embodiments, the splittable member 350 is split apart without causing the lead to move.

Once the lead is positioned at the target stimulation location, the lead may be coupled to a control module (e.g., 102 of FIG. 1) and implanted using well-known techniques, for example, using one or more tunneling straws placed in passageways underneath patient skin with bores that are sized large enough to receive the lead. In at least some embodiments, the lead is coupled directly to a connector of a control module. In other embodiments, the lead is coupled to the control module via one or more other devices, including an adaptor, a lead extension, an operating room cable, or the like or combinations thereof.

Figure 13:
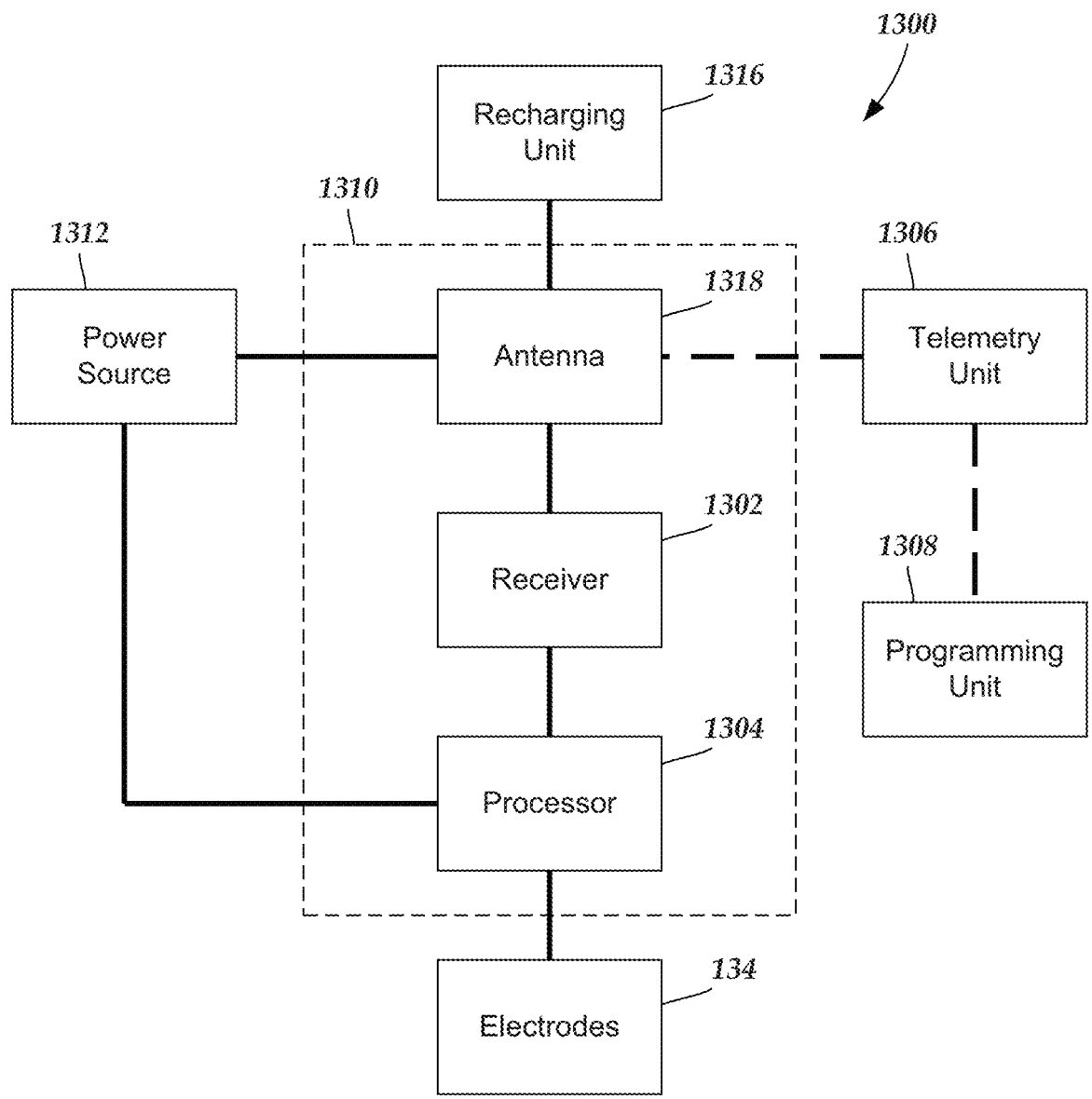
FIG. 13 is a schematic overview of one embodiment of components of a stimulation system, including an electronic subassembly disposed within a control module, according to the invention.

FIG. 13 is a schematic overview of one embodiment of components of an electrical stimulation system 1300 including an electronic subassembly 1310 disposed within a control module. It will be understood that the electrical stimulation system can include more, fewer, or different components and can have a variety of different configurations including those configurations disclosed in the stimulator references cited herein.

Some of the components (for example, a power source 1312, an antenna 1318, a receiver 1302, and a processor 1304) of the electrical stimulation system can be positioned on one or more circuit boards or similar carriers within a sealed housing of an implantable pulse generator, if desired. Any power source 1312 can be used including, for example, a battery such as a primary battery or a rechargeable battery. Examples of other power sources include super capacitors, nuclear or atomic batteries, mechanical resonators, infrared collectors, thermally powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1318 or a secondary antenna. The external power source can be in a device that is mounted on the skin of the user or in a unit that is provided near the user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 selects which electrode(s) are cathodes and which electrode(s) are anodes. In some embodiments, the processor 1304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306 which is programmed by the programming unit 1308. The programming unit 1308 can be external to, or part of, the telemetry unit 1306. The telemetry unit 1306 can be a device that is worn on the skin of the user or can be carried by the user and can have a form similar to a pager, cellular phone, or remote control, if desired. As another alternative, the telemetry unit 1306 may not be worn or carried by the user but may only be available at a home station or at a clinician's office. The programming unit 1308 can be any unit that can provide information to the telemetry unit 1306 for transmission to the electrical stimulation system 1300. The programming unit 1308 can be part of the telemetry unit 1306 or can provide signals or information to the telemetry unit 1306 via a wireless or wired connection. One example of a suitable programming unit is a computer operated by the user or clinician to send signals to the telemetry unit 1306.

The signals sent to the processor 1304 via the antenna 1318 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include the antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306 or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead introducer comprising:
   an outer needle comprising an outer needle body and an outer needle hub coupled to the outer needle body, the outer needle body defining a channel extending along a longitudinal length of the outer needle body, and
   an inner needle comprising an inner needle body configured for sliding along the channel of the outer needle body and an inner needle hub coupled to the inner needle body, the inner needle body defining a lumen extending along a longitudinal length of the inner needle body; and
   a splittable member comprising a splittable member body and a splittable member hub and having a distal end, the splittable member defining a longitudinal axis and configured for disposing over the outer needle body, wherein the splittable member hub comprises a splittable hub body and two pull-apart tabs, wherein the splittable hub body comprises a transverse proximal face defining an opening and the two pull-apart tabs extend in a proximal direction from the transverse proximal face of the splittable hub body, wherein the splittable member is configured for separating longitudinally by pulling the two pull-apart tabs away from each other.

2. The lead introducer of claim 1, wherein the two pull-apart tabs extend parallel to the longitudinal axis of the splittable member.

3. The lead introducer of claim 1, wherein the inner needle hub comprises a collar defining one or more openings, wherein the one or more openings are configured to receive a portion of the two pull-apart tabs within the one or more openings to prevent inadvertently pulling the two pull-apart tabs away from each other.

4. The lead introducer of claim 1, wherein the outer needle hub comprises a collar defining one or more openings, wherein the one or more openings are configured to receive a portion of the two pull-apart tabs within the one or more openings to prevent inadvertently pulling the two pull-apart tabs away from each other.

5. The lead introducer of claim 1, further comprising a stylet configured for sliding along the lumen of the inner needle body.

6. The lead introducer of claim 5, wherein the stylet comprises a stylet hub with projections disposed on a distal portion of the stylet hub and defining one or more cavities to receive a portion of the two pull apart tabs.

7. The lead introducer of claim 1, wherein the splittable member hub is configured to receive at least portions of both the inner needle hub and the outer needle hub within the splittable member hub.

8. The lead introducer of claim 7, further comprising an annular seal member formed by either a) the inner needle hub or b) a combination of the inner needle hub and outer needle hub, wherein the annular seal member is configured to form a fluid-resisting seal with an interior surface of the splittable member hub when portions of the inner needle hub and outer needle hub are received within the splittable member hub.

9. An insertion kit comprising:
   the lead introducer of claim 1; and
   a neurostimulation lead configured for implantation into a patient, the neurostimulation lead comprising a lead body having a distal end portion and a proximal end portion,
a plurality of electrodes disposed at the distal end portion of the lead body,
a plurality of terminals disposed at the proximal end portion of the lead body, and
a plurality of conductive wires coupling the electrodes electrically to the terminals;
wherein the channel of the outer needle body is configured such that, when the inner needle of the lead introducer is not inserted in the channel, the distal end portion of the lead body is insertable into the channel with the lead body being laterally separatable from the outer needle of the lead introducer through the channel of the outer needle body.

10. An electrical stimulation system comprising:
the insertion kit of claim 9;
a control module configured to electrically couple to the neurostimulation lead of the insertion kit, the control module comprising
a housing, and
an electronic subassembly disposed in the housing; and
a connector for receiving the neurostimulation lead, the connector comprising
a connector housing defining a port for receiving the proximal end portion of the lead body, and
a plurality of connector contacts disposed in the connector housing, the connector contacts configured to couple to the terminals of the neurostimulation lead when the proximal end portion of the lead body of the neurostimulation lead is received by the connector housing.

11. A method for implanting a neurostimulation lead into a patient, the method comprising:
advancing the lead introducer of claim 1 into the patient;
removing the inner needle of the lead introducer from the patient, leaving the outer needle and splittable member of the lead introducer within the patient;
inserting into the channel of the outer needle body a distal end portion of a neurostimulation lead, the neurostimulation lead comprising a plurality of electrodes disposed along a distal end portion of the neurostimulation lead and a plurality of terminals disposed along a proximal end portion of the neurostimulation lead;
separating the splittable member into at least two parts along a length of the splittable member; and
removing the outer needle and the splittable member from the patient, leaving the neurostimulation lead implanted in the patient at a target stimulation location.

12. A lead introducer comprising:
an outer needle comprising an outer needle body and an outer needle hub coupled to the outer needle body, the outer needle body defining a channel extending along a longitudinal length of the outer needle body, and
an inner needle comprising an inner needle body configured for sliding along the channel of the outer needle body and an inner needle hub coupled to the inner needle body, the inner needle body defining a lumen extending along a longitudinal length of the inner needle body;
a splittable member comprising a splittable member body and a splittable member hub and having a distal end, the splittable member configured for disposing over the outer needle body and for being longitudinally splittable, wherein the splittable member hub is configured to receive at least a portion of the inner needle hub within the splittable member hub; and
an annular seal member formed by the inner needle hub, wherein the annular seal member is configured to form a fluid-resisting seal with the splittable member hub when the portion of the inner needle hub is received within the splittable member hub.

13. The lead introducer of claim 12, wherein the annular seal member comprises an O-ring disposed along a distal portion of the inner needle hub.

14. A method for implanting a neurostimulation lead into a patient, the method comprising:
advancing the lead introducer of claim 12 into the patient;
removing the inner needle of the lead introducer from the patient, leaving the outer needle and splittable member of the lead introducer within the patient;
inserting into the channel of the outer needle body a distal end portion of a neurostimulation lead, the neurostimulation lead comprising a plurality of electrodes disposed along a distal end portion of the neurostimulation lead and a plurality of terminals disposed along a proximal end portion of the neurostimulation lead;
separating the splittable member into at least two parts along a length of the splittable member; and
removing the outer needle and the splittable member from the patient, leaving the neurostimulation lead implanted in the patient at a target stimulation location.

15. A lead introducer comprising:
an outer needle comprising an outer needle body and an outer needle hub coupled to the outer needle body, the outer needle body defining a channel extending along a longitudinal length of the outer needle body, and
an inner needle comprising an inner needle body configured for sliding along the channel of the outer needle body and an inner needle hub coupled to the inner needle body, the inner needle body defining a lumen extending along a longitudinal length of the inner needle body;
a splittable member comprising a splittable member body and a splittable member hub and having a distal end, the splittable member configured for disposing over the outer needle body and the inner needle body and for being longitudinally splittable, wherein the splittable member hub is configured to receive at least a portion of both the inner needle hub and the outer needle hub within the splittable member hub; and
an annular seal member formed by a combination of the inner needle hub and the outer needle hub, wherein the annular seal member is configured to form a fluid-resisting seal with the splittable member hub when the portions of the inner needle hub and outer needle hub are received within the splittable member hub.

16. The lead introducer of claim 15, wherein the annular seal member comprises an O-ring disposed along a distal portion of the inner needle hub and an annular detent defined by the outer needle hub, wherein the splittable member hub comprises a ridged structure configured to mate with the annular detent.

17. The lead introducer of claim 15, wherein the inner needle hub comprises a seal element comprising a wedge and a partial seal rib defined at a distal end of the wedge.

18. The lead introducer of claim 17, wherein the outer needle hub further comprises a seal rib that, when mated with the partial seal rib of the inner needle hub, forms the annular seal member.

19. The lead introducer of claim 17, wherein the outer needle hub defines a wedge-shaped opening configured to mate with the wedge of the seal element of the inner needle hub.

20. The lead introducer of claim 17, wherein the seal element of the inner needle hub has a conical shape except for the wedge.

* * * * *